(12) United States Patent
Zubiate et al.

(10) Patent No.: US 10,166,682 B2
(45) Date of Patent: Jan. 1, 2019

(54) SYSTEM FOR RELEASABLY ATTACHING A DISPOSABLE DEVICE TO A DURABLE DEVICE

(71) Applicant: Carnegie Mellon University, Pittsburgh, PA (US)

(72) Inventors: Brett Zubiate, Duxbury, MA (US); Amir Degani, Pittsburgh, PA (US); Howie Choset, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 839 days.

(21) Appl. No.: 13/895,669

(22) Filed: May 16, 2013

(65) Prior Publication Data

US 2013/0319159 A1 Dec. 5, 2013

Related U.S. Application Data

(63) Continuation of application No. 12/038,691, filed on Feb. 27, 2008, now Pat. No. 8,459,138.
(Continued)

(51) Int. Cl.
*B25J 9/06* (2006.01)
*B25J 13/02* (2006.01)
(Continued)

(52) U.S. Cl.
CPC ............. *B25J 13/025* (2013.01); *B25J 9/06* (2013.01); *B25J 9/065* (2013.01); *B25J 13/085* (2013.01);
(Continued)

(58) Field of Classification Search
CPC .. B25J 9/06; B25J 18/16; A61B 1/005; A61B 1/0055; A61B 1/0057; A61B 1/00128;
(Continued)

(56) References Cited

U.S. PATENT DOCUMENTS 3,060,972 A 10/1962 Sheldon
3,190,286 A 6/1965 Stokes
(Continued)

FOREIGN PATENT DOCUMENTS

EP 0 427 949 * 5/1991
EP 1884185 A1 2/2008
(Continued)

OTHER PUBLICATIONS

Shammas et al., "New Joint Design for Three-dimensional Hyper Redundant Robots," International Conference on Robots and Systems, Las Vegas, NV, Oct. 2003.
(Continued)

*Primary Examiner* — William C Joyce
(74) *Attorney, Agent, or Firm* — Fox Rothschild LLP

(57) ABSTRACT

A system for releasably attaching a steerable disposable multi-linked device to a durable device may include a disposable portion and a durable portion. The disposable portion may include a connecting member connected to the disposable portion and the durable portion and a steerable multi-linked device. The steerable multi-linked device may include a first link, a plurality of intermediate links, a second link movably coupled to a second one of the intermediate links, and a cable which passes through the first link and intermediate links and extends beyond a first end of the first link. A first one of the intermediate links may be movably coupled to the first link. The durable portion may include an axial member which defines an opening therethrough and a feeder mechanism.

7 Claims, 34 Drawing Sheets

Related U.S. Application Data

(60) Provisional application No. 60/891,881, filed on Feb. 27, 2007.

(51) Int. Cl.
    *B25J 18/06*     (2006.01)
    *B25J 13/08*     (2006.01)
    *A61B 17/00*     (2006.01)
    *A61B 1/00*     (2006.01)

(52) U.S. Cl.
    CPC ........... *B25J 18/06* (2013.01); *A61B 1/00128* (2013.01); *A61B 17/00234* (2013.01); *A61B 2017/0023* (2013.01); *A61B 2017/00477* (2013.01); *F16B 2200/10* (2018.08); *Y10S 901/15* (2013.01); *Y10S 901/21* (2013.01); *Y10S 901/28* (2013.01); *Y10T 74/20* (2015.01); *Y10T 74/20201* (2015.01); *Y10T 74/20305* (2015.01); *Y10T 74/20323* (2015.01); *Y10T 74/20329* (2015.01); *Y10T 403/7039* (2015.01)

(58) Field of Classification Search
    CPC ...... A61B 17/00234; A61B 2017/0023; A61B 2017/00477
    USPC ........ 74/490.04; 901/21; 600/140, 141, 142, 600/146; 606/1, 108, 130
See application file for complete search history.

(56) References Cited

U.S. PATENT DOCUMENTS

| | | | |
|---|---|---|---|
| 3,643,653 A | 2/1972 | Takahashi et al. | |
| 4,686,963 A | 8/1987 | Cohen et al. | |
| 4,850,351 A | 7/1989 | Herman et al. | |
| 5,005,558 A | 4/1991 | Aomori | |
| 5,143,475 A | 9/1992 | Chikama | |
| 5,251,611 A | 10/1993 | Zehel et al. | |
| 5,257,618 A | 11/1993 | Kondo | |
| 5,318,526 A | 6/1994 | Cohen | |
| 5,327,905 A | 7/1994 | Avitall | |
| 5,337,733 A | 8/1994 | Bauerfeind et al. | |
| 5,386,741 A | 2/1995 | Rennex | |
| 5,415,158 A | 5/1995 | Barthel et al. | |
| 5,467,763 A | 11/1995 | McMahon et al. | |
| 5,472,017 A | 12/1995 | Kovalcheck | |
| 5,483,951 A | 1/1996 | Frassica et al. | |
| 5,514,157 A | 5/1996 | Nicholas et al. | |
| 5,531,715 A | 7/1996 | Engelson et al. | |
| 5,549,542 A | 8/1996 | Kovalcheck | |
| 5,587,937 A | 12/1996 | Massie et al. | |
| 5,605,543 A | 2/1997 | Swanson | |
| 5,662,587 A | 9/1997 | Grundfest et al. | |
| 5,743,876 A | 4/1998 | Swanson | |
| 5,749,828 A | 5/1998 | Solomon et al. | |
| 5,759,151 A | 6/1998 | Sturges | |
| 5,810,716 A | 9/1998 | Mukherjee et al. | |
| 5,868,760 A | 2/1999 | McGuckin, Jr. | |
| 5,907,487 A | 5/1999 | Rosenberg et al. | |
| 5,947,996 A | 9/1999 | Logeman | |
| 6,036,677 A | 3/2000 | Javier, Jr. et al. | |
| 6,197,017 B1 | 3/2001 | Brock et al. | |
| 6,221,061 B1 | 4/2001 | Engelson et al. | |
| 6,341,201 B1 | 1/2002 | Ishiguro et al. | |
| 6,364,828 B1 | 4/2002 | Yeung et al. | |
| 6,432,112 B2 | 8/2002 | Brock et al. | |
| 6,517,477 B1 | 2/2003 | Wendlandt | |
| 6,554,844 B2 | 4/2003 | Lee et al. | |
| 6,610,007 B2 | 8/2003 | Belson et al. | |
| 6,623,448 B2 | 9/2003 | Slater | |
| 6,638,266 B2 | 10/2003 | Wilson et al. | |
| 6,682,493 B2 | 1/2004 | Mirigian | |
| 6,692,485 B1 | 2/2004 | Brock et al. | |
| 6,697,048 B2 | 2/2004 | Rosenberg et al. | |
| 6,730,020 B2 | 5/2004 | Peng et al. | |
| 6,743,239 B1 | 6/2004 | Kuehn et al. | |
| 6,790,173 B2 | 9/2004 | Saadat et al. | |
| 6,800,056 B2 | 10/2004 | Tartaglia et al. | |
| 6,827,710 B1 | 12/2004 | Mooney et al. | |
| 6,837,846 B2 | 1/2005 | Jaffe et al. | |
| 6,837,847 B2 | 1/2005 | Ewers et al. | |
| 6,858,005 B2 | 2/2005 | Ohline et al. | |
| 6,869,396 B2 | 3/2005 | Belson | |
| 6,890,297 B2 | 5/2005 | Belson | |
| 6,899,673 B2 | 5/2005 | Ogura et al. | |
| 6,907,298 B2 | 6/2005 | Smits et al. | |
| 6,921,363 B2 | 7/2005 | Knowles | |
| 6,960,162 B2 | 11/2005 | Saadat et al. | |
| 6,960,163 B2 | 11/2005 | Ewers et al. | |
| 6,963,792 B1 | 11/2005 | Green | |
| 6,974,411 B2 | 12/2005 | Belson | |
| 6,976,991 B2 | 12/2005 | Hebert et al. | |
| 6,984,203 B2 | 1/2006 | Tartaglia et al. | |
| 7,029,435 B2 | 4/2006 | Nakao | |
| 7,041,052 B2 | 5/2006 | Saadat et al. | |
| 7,044,907 B2 | 5/2006 | Belson | |
| 7,087,013 B2 | 8/2006 | Belson et al. | |
| 7,090,637 B2 | 8/2006 | Danitz et al. | |
| 7,090,683 B2 | 8/2006 | Brock et al. | |
| 7,108,688 B2 | 9/2006 | Jensen | |
| 7,128,708 B2 | 10/2006 | Saadat et al. | |
| 7,169,141 B2 | 1/2007 | Brock et al. | |
| 7,171,279 B2 | 1/2007 | Buckingham et al. | |
| 7,182,731 B2 | 2/2007 | Nguyen et al. | |
| 7,209,344 B2 | 4/2007 | Hillman et al. | |
| 7,214,230 B2 | 5/2007 | Brock et al. | |
| 7,232,434 B2 | 6/2007 | Suyama et al. | |
| 7,250,027 B2 | 7/2007 | Barry | |
| 7,322,935 B2 | 1/2008 | Palmer et al. | |
| 7,338,505 B2 | 3/2008 | Belson | |
| 7,387,046 B2 | 6/2008 | Ikeda et al. | |
| 7,543,518 B2 | 6/2009 | Buckingham et al. | |
| 7,670,284 B2 | 3/2010 | Padget et al. | |
| 7,682,319 B2 | 3/2010 | Martin et al. | |
| 7,811,277 B2 | 10/2010 | Boulais | |
| 8,052,597 B2 | 11/2011 | Boulais | |
| 8,100,031 B2 | 1/2012 | Zubiate et al. | |
| 8,192,422 B2 | 6/2012 | Zubiate et al. | |
| 2002/0087048 A1 | 7/2002 | Brock et al. | |
| 2002/0087049 A1* | 7/2002 | Brock ................ | A61B 17/0469 600/114 |
| 2002/0108644 A1 | 8/2002 | Hoadley et al. | |
| 2005/0119527 A1 | 6/2005 | Banik et al. | |
| 2005/0131279 A1 | 6/2005 | Boulais et al. | |
| 2005/0240078 A1 | 10/2005 | Kwon et al. | |
| 2006/0052664 A1 | 3/2006 | Julian et al. | |
| 2006/0058582 A1 | 3/2006 | Maahs et al. | |
| 2006/0161045 A1 | 7/2006 | Merril et al. | |
| 2006/0178560 A1 | 8/2006 | Saadat et al. | |
| 2007/0043259 A1 | 2/2007 | Jaffe et al. | |
| 2008/0039690 A1 | 2/2008 | Zubiate et al. | |
| 2008/0125794 A1 | 5/2008 | Brock et al. | |
| 2008/0132913 A1 | 6/2008 | Brock et al. | |
| 2008/0177285 A1 | 7/2008 | Brock et al. | |
| 2008/0205980 A1 | 8/2008 | Zubiate et al. | |
| 2009/0069842 A1 | 3/2009 | Lee et al. | |
| 2009/0171147 A1 | 7/2009 | Lee et al. | |
| 2009/0171151 A1 | 7/2009 | Choset et al. | |

FOREIGN PATENT DOCUMENTS

| | | |
|---|---|---|
| EP | 1927312 A1 | 6/2008 |
| WO | WO-9405200 A1 | 3/1994 |
| WO | WO-9501751 A1 | 1/1995 |
| WO | WO-2006083306 A2 | 8/2006 |

OTHER PUBLICATIONS

Brown et al., "Design and Control of a Second-Generation Hyper-Redundant Mechanism," International Conference on Robots and Systems, San Diego, CA, Oct. 29-Nov. 2, 2007.

(56) References Cited

OTHER PUBLICATIONS

Wolfe et al., "A Mobile Hyper Redundant Mechanism for Search and Rescue Tasks," International Conference on Robots and Systems, Las Vegas, NV, Oct. 2003.

* cited by examiner

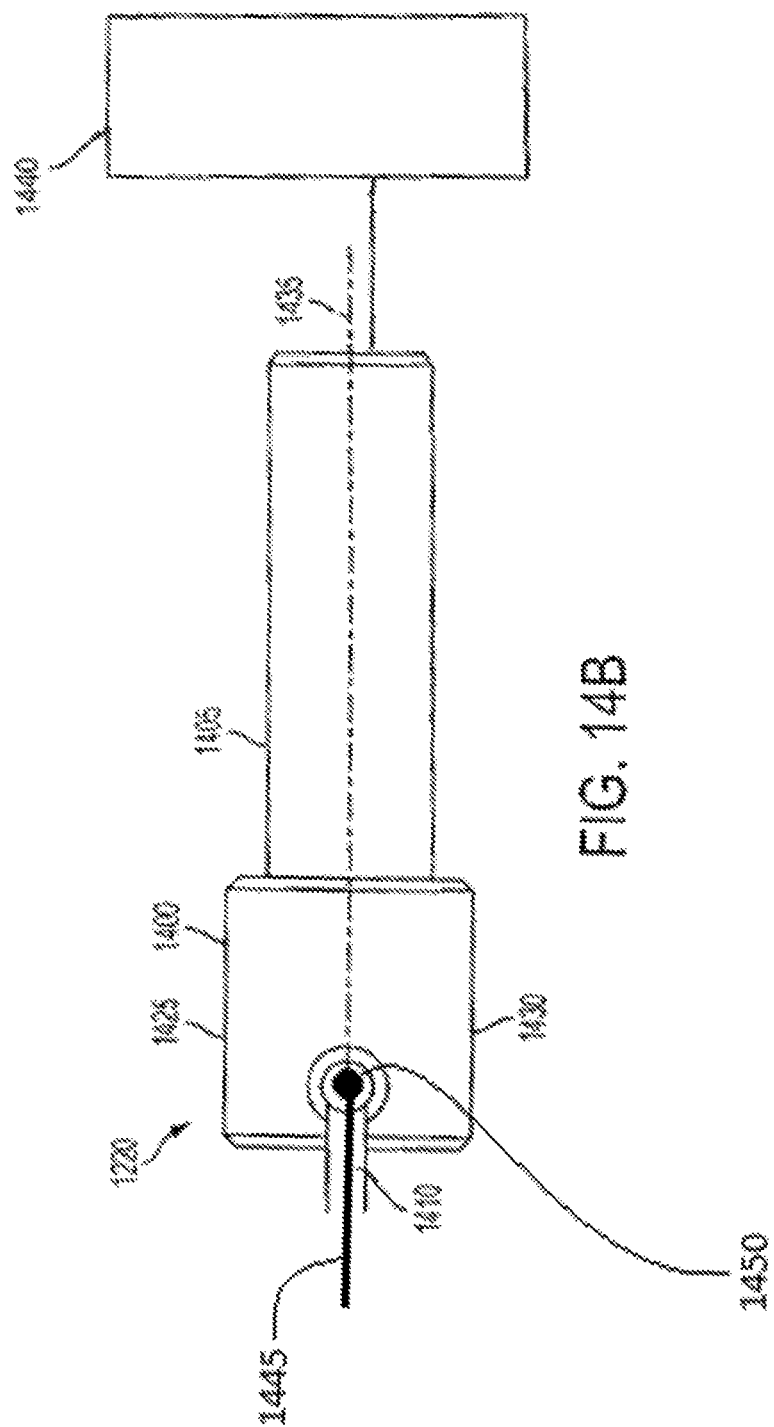

SYSTEM FOR RELEASABLY ATTACHING A DISPOSABLE DEVICE TO A DURABLE DEVICE

CROSS REFERENCE TO RELATED APPLICATIONS

This application is a continuation of and claims priority to U.S. patent application Ser. No. 12/038,691, filed on Feb. 27, 2008, which claims priority to U.S. Patent Application 60/891,881 filed Feb. 27, 2007, the entireties of which are incorporated by reference herein. U.S. patent application Ser. No. 12/038,691 is related to U.S. patent application Ser. No. 12/038,560, filed Feb. 27, 2008, now U.S. Pat. No. 8,100,031, and U.S. patent application Ser. No. 12/038,729, filed Feb. 27, 2008.

Not Applicable

BACKGROUND

This application discloses an invention that is related, generally and in various embodiments, to a system for releasably attaching a disposable device to a durable device.

SUMMARY

A system for releasably attaching a steerable disposable multi-linked device to a durable device may include a disposable portion and a durable portion. The disposable portion may include a connecting member connected to the disposable portion and the durable portion and a steerable multi-linked device. The steerable multi-linked device may include a first link, a plurality of intermediate links, a second link movably coupled to a second one of the intermediate links, and a cable which passes through the first link and intermediate links and extends beyond a first end of the first link. A first one of the intermediate links may be movably coupled to the first link. The durable portion may include an axial member which defines an opening therethrough and a feeder mechanism.

BRIEF DESCRIPTION OF DRAWINGS

Various embodiments of the invention are described herein by way of example in conjunction with the following figures.

FIGS. 14A-14C illustrate an exemplary axial member according to various embodiments.

DETAILED DESCRIPTION

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

According to various embodiments, the invention described herein may be utilized to control movement of a multi-linked device such as the steerable multi-linked device described herein. For ease of explanation purposes, the invention will be described in the context of its use with various embodiments of the steerable multi-linked device described herein. However, one skilled in the art will appreciate that the invention may be utilized with other types of multi-linked devices.

Figure 1A:
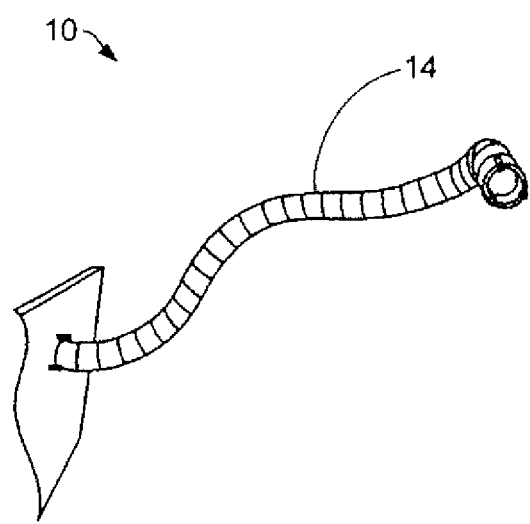
FIGS. 1A and 1B illustrate various embodiments of a steerable multi-linked device.
Figure 1B:
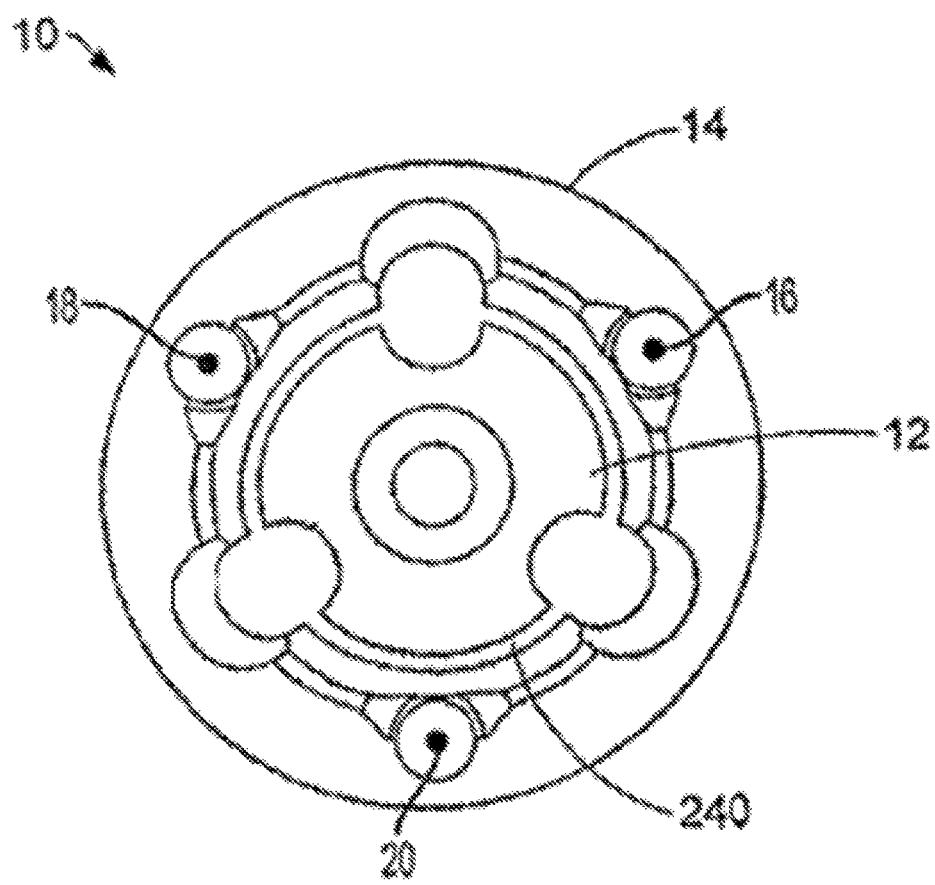

FIGS. 1A and 1B illustrate various embodiments of a steerable multi-linked device 10. According to various embodiments, the steerable multi-linked device may be a snake robot, a continuum robot or the like. Various embodiments of the device 10 may be utilized for medical procedures (e.g., as a robotic bore, positioning device, ablation tool, camera or instrument support, or guidance system for minimally invasive procedures), for surveillance applications, for inspection applications, for search and rescue applications, etc. For purposes of clarity only, the utility of the device 10 will be described hereinbelow in the context of its applicability to medical procedures. However, a person skilled in the art will appreciate that the device 10 can be utilized in a variety of different applications.

The device 10 comprises a first mechanism 12 and a second mechanism 14. According to various embodiments, a mechanism may be a snake robot, a continuum robot or the like. According to various embodiments, the second mechanism 14 is structured and arranged to receive and surround the first mechanism 12 as shown in FIG. 1B. Thus, the first mechanism and second mechanism may be concentric. For such embodiments, the first mechanism 12 may be considered the inner mechanism or the core mechanism, and the second mechanism 14 may be considered the outer mechanism or the sleeve mechanism. According to other embodiments, the first and second mechanisms 12, 14 may be structured and arranged to have a relationship other than a concentric relationship. For example, one skilled in the art will appreciate that, according to various embodiments, the first and second mechanisms 12, 14 may be structured and arranged to operate in a side-by-side arrangement, where the first mechanism 12 operates adjacent to the second mechanism 14. According to various embodiments, additional and/or alternate configurations may be used within the scope of this disclosure. According to various embodiments, a three-dimensional space 240 may be provided between the first and second mechanisms. This space will be described in more detail below.

As described in more detail hereinbelow, the first mechanism 12 may operate in either a rigid mode or a limp mode, the second mechanism 14 may operate in either a rigid mode or a limp mode, and the first and second mechanisms 12, 14 may operate independent of one another. Both the first mechanism 12 and the second mechanism 14 may be steerable mechanisms. Accordingly, it will be appreciated that the device 10 may be utilized to navigate a luminal space as well as any three-dimensional path within an intracavity space. According to various embodiments, the device 10 may advance by alternating the operation of the first mechanism 12 and the second mechanism 14 between a limp mode and a rigid mode.

According to various embodiments, the device 10 may also comprise one or more cables. According to various embodiments, one or more of the cables may be steering cables and/or tensioning cables. For example, the device may include three steering cables and one tensioning cables.

Figure 2:
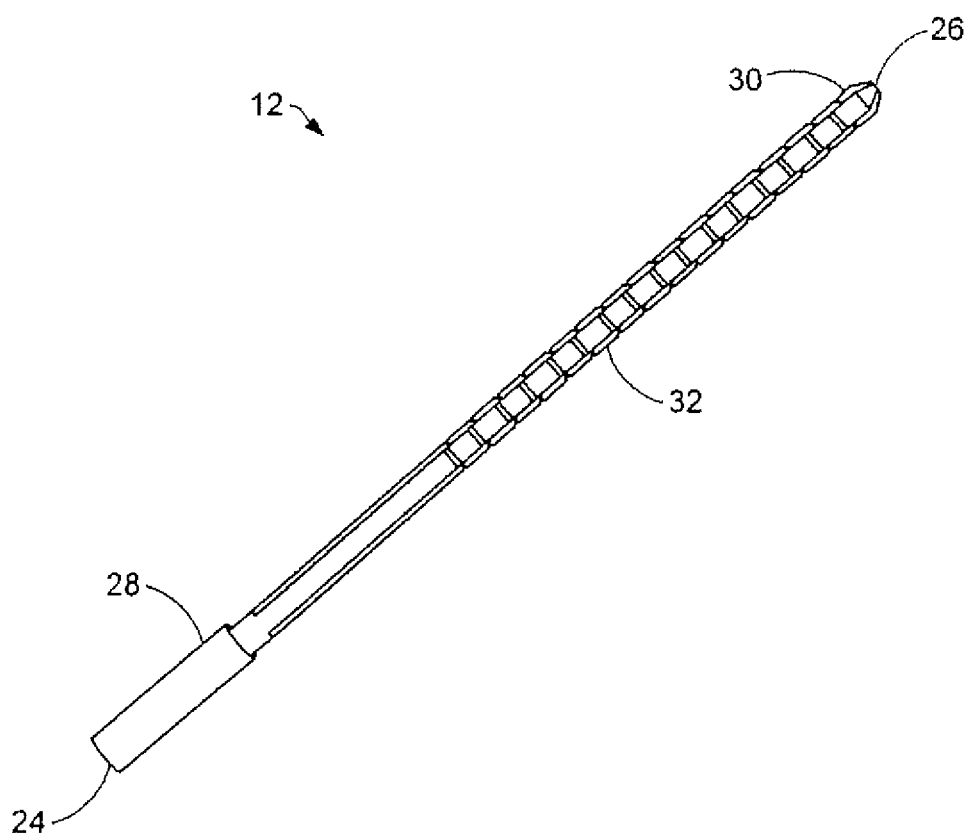
FIG. 2 illustrates various embodiments of a core mechanism of the device of FIG. 1.

FIG. 2 illustrates various embodiments of the first mechanism 12 of the device 10. The first mechanism 12 is a multi-linked mechanism and includes a first end 24 and a second end 26. The first end 24 may be considered the proximal end and the second end 26 may be considered the distal end. The first mechanism 12 may comprise a first link 28, a second link 30, and one or more intermediate links 32 between the first and second links 28, 30. The first link 28 may be considered the proximal link, and the second link 30 may be considered the distal link.

Figure 3A:
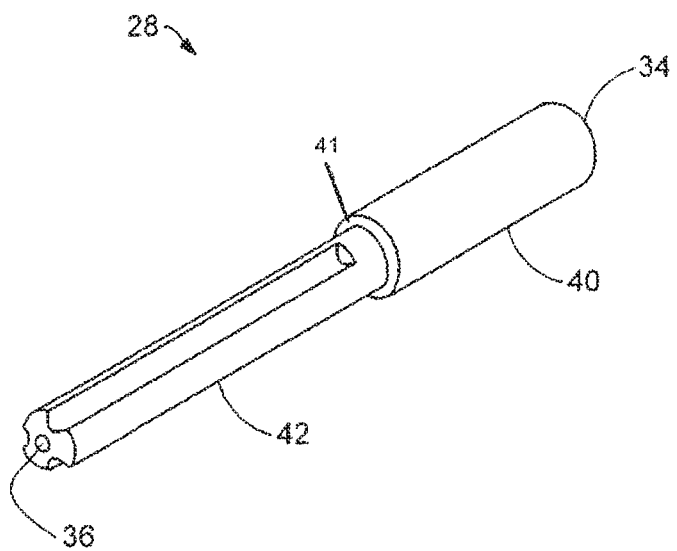
FIGS. 3A-3C illustrate various embodiments of a proximal link of the core mechanism.
Figure 3B:
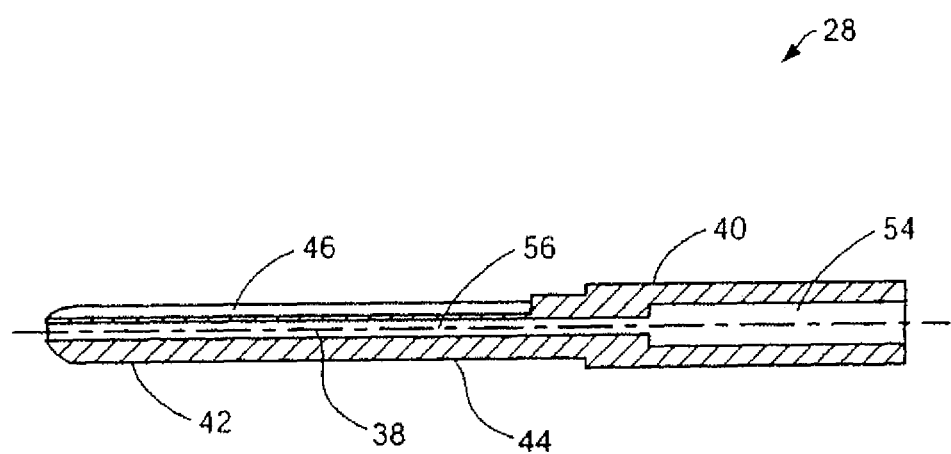
Figure 3C:
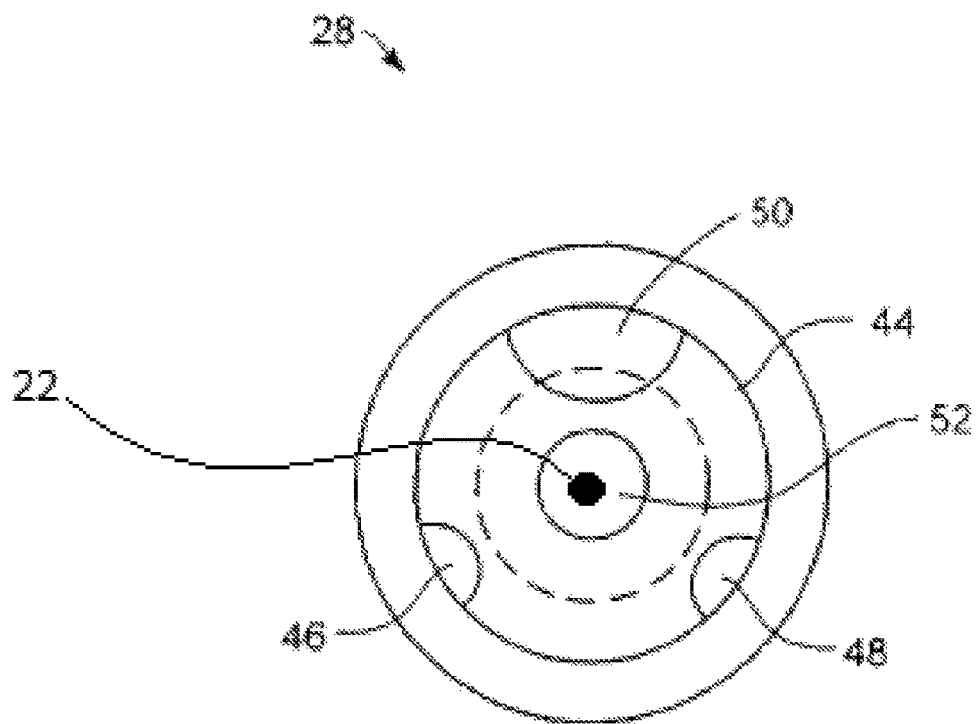

FIGS. 3A-3C illustrate various embodiments of the first link 28 (inner proximal link) of the first mechanism 12. The first link 28 includes a first end 34 and a second end 36, and defines a longitudinal axis 38 that passes through the center of the first end 34 and the center of the second end 36 as shown in FIG. 3B. The first link 28 may be fabricated from any suitable material. According to various embodiments, the first link 28 is fabricated from a fiber reinforced material such as, for example, G10/FR4 Garolite®. The first link 28 has a generally cylindrical shaped exterior and is described in more detail hereinbelow.

The first link 28 comprises a first portion 40 and a second portion 42. The first portion 40 may be considered the proximal portion and the second portion 42 may be considered the distal portion. The first portion 40 may be fabricated integral with the second portion 42. The first portion 40 has a cylindrical shaped exterior, and extends from the first end 34 of the first link 28 toward the second end 36 of the first link 28. According to various embodiments, the diameter of the first portion 40 may be on the order of approximately 6.35 millimeters. Other sizes are possible.

The second portion 42 has a generally cylindrically shaped exterior, with other features described below. The second portion 42 has a cylindrically shaped exterior where it contacts the first portion 40, and tapers toward the second end 36 of the first link 28. The second portion 42 may be shaped in the form of a generally segmented hemisphere at the second end 36 of the first link 28. According to various embodiments, the diameter of the second portion 42 may be on the order of approximately 4.75 millimeters where it contacts the first portion 40. Other sizes are possible.

The second portion 42 comprises a first surface 44. The first surface 44 may be considered the outer surface of the second portion 42. The second portion 42 defines a first groove 46 parallel to the longitudinal axis 38 along the first surface 44, a second groove 48 parallel to the longitudinal axis 38 along the first surface 44, and a third groove 50 parallel to the longitudinal axis 38 along the first surface 44. Each of the first, second and third grooves 46, 48, 50 extend along the first surface 44 toward the second end 36 of the first link 28. The first, second and third grooves 46, 48, 50 may be semi-tubular shaped and may be evenly spaced about the first surface 44 of the second portion 42 of the first link 28 as shown in FIG. 3C. According to various embodiments, the first, second, and third grooves 46, 48, 50 may be configured in the shape of a segmented cylinder. The size of each of the grooves 46, 48, 50 may be identical to one another or may be different from one another. For example, according to various embodiments, the first and second grooves 46, 48 may be configured as segments of a cylinder having a diameter on the order of approximately 1.25 millimeters, and the third groove 50 may be configured as a segment of a cylinder having a diameter on the order of approximately 2.50 millimeters. The length of the first link 28 may be on the order of approximately 65 millimeters. However, one skilled in the art will appreciate that the length or diameter of the first link 28 can vary based on the application.

The first link 28 also defines a passage 52 extending from the first end 34 to the second end 36 along the longitudinal axis 38 as shown in FIG. 3B. The passage 52 is of a size sufficient to allow at least one cable to pass therethrough. According to various embodiments, the passage 52 may be of a sufficient size to allow a tensioning cable 22 to pass therethrough. According to various embodiments, the passage 52 is generally configured as a complex shape that comprises a combination of a first cylinder 54 that extends from the first end 34 toward the second end 36, and a second cylinder 56 that extends from the first cylinder 54 toward the second end 36. The diameter of the first cylinder 54 is larger than the diameter of the second cylinder 56. For example, according to various embodiments, the first cylinder 54 may have a diameter on the order of approximately 3.20 millimeters and the second cylinder 56 may have a diameter on the order of approximately 1.50 millimeters. Other sizes are possible.

Figure 4A:
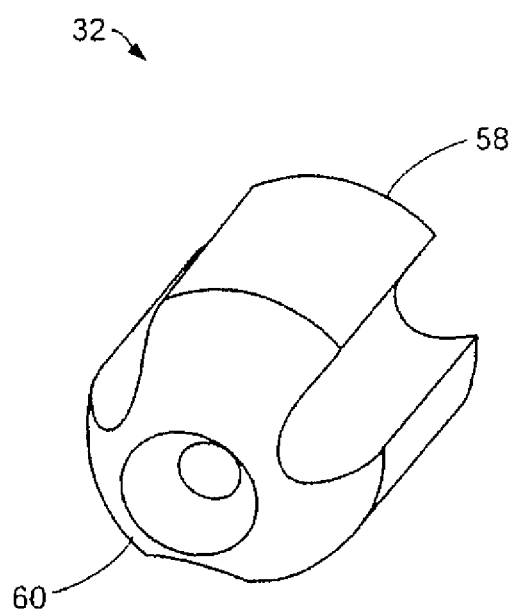
FIGS. 4A-4C illustrate various embodiments of an intermediate link of the core mechanism.
Figure 4B:
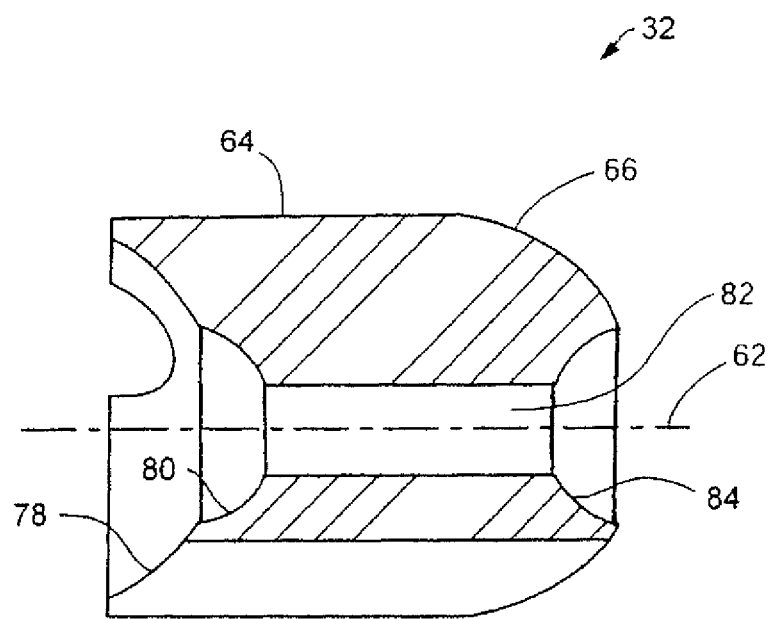
Figure 4C:
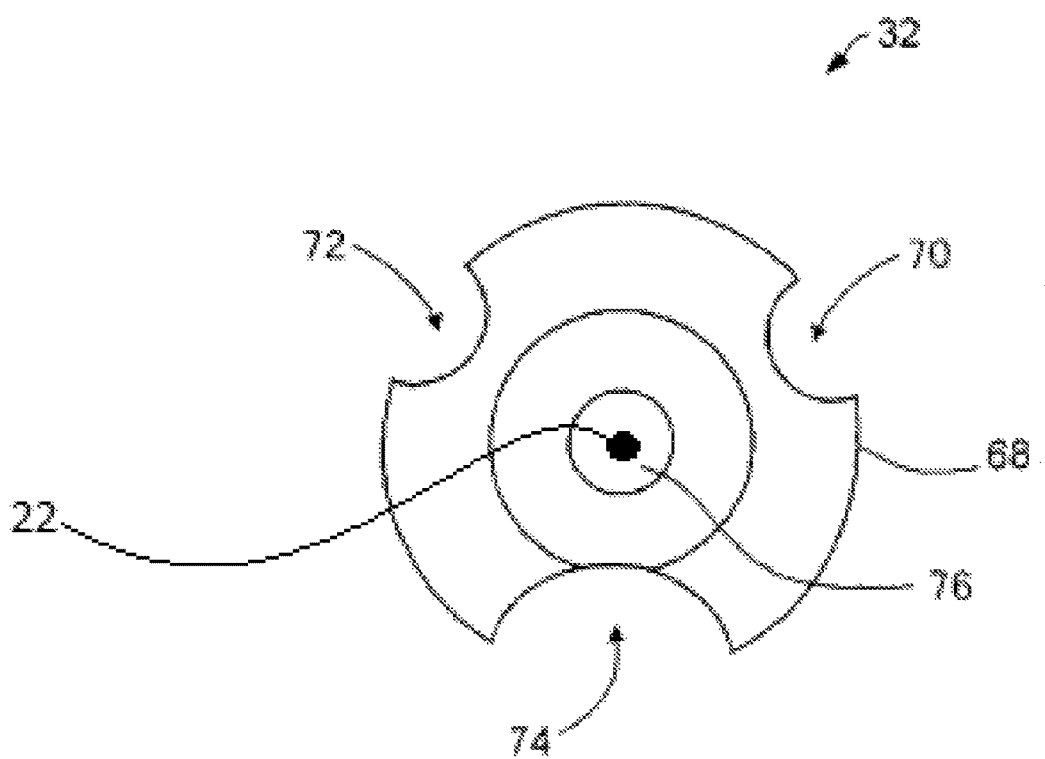

FIGS. 4A-4C illustrate various embodiments of one of the intermediate links 32 (inner intermediate link) of the first mechanism 12. The intermediate link 32 is representative of the other intermediate links 32. The intermediate link 32 includes a first end 58 and a second end 60, and defines a longitudinal axis 62 that passes through the center of the first end 58 and the center of the second end 60 as shown in FIG. 4B. The intermediate link 32 may be fabricated from any suitable material. According to various embodiments, the intermediate link 32 is fabricated from a fiber reinforced material such as, for example, G10/FR4 Garolite®. The intermediate link 32 has a generally bullet-shaped exterior and is described in more detail hereinbelow.

The intermediate link 32 comprises a first portion 64 and a second portion 66. The first portion 64 may be considered the proximal portion and the second portion 66 may be considered the distal portion. The first portion 64 may be fabricated integral with the second portion 66. The first portion 64 has a generally cylindrical shaped exterior, and extends from the first end 58 of the intermediate link 32 toward the second end 60 of the intermediate link 32. According to various embodiments, the second portion 66 has a generally cylindrically shaped exterior where it contacts the first portion 64, and tapers toward the second end 60 of the intermediate link 32. The exterior of the second portion 66 is configured in the form of a generally segmented hemisphere. According to various embodiments, the diameter of the intermediate link 32 may be on the order of approximately 4.75 millimeters at the first end 58 thereof. The length of the intermediate link 32 may be on the order of approximately 5.85 millimeters. However, one skilled in the art will appreciate that the length or diameter of the intermediate link 32 can vary based on the application.

The intermediate link 32 also comprises a first surface 68 that extends from the first end 58 of the intermediate link 32 to the second end 60 of the intermediate link 32. The first surface 68 may be considered the outer surface of the intermediate link 32. The intermediate link 32 also defines a first groove 70 parallel to the longitudinal axis 62 along the first surface 68, a second groove 72 parallel to the longitudinal axis 62 along the first surface 68, and a third groove 74 parallel to the longitudinal axis 62 along the first surface 68. Each of the first, second and third grooves 70, 72, 74 extend along the first surface 68 from the first end 58 of the intermediate link 32 toward the second end 60 of the intermediate link 32. The first, second and third grooves 70, 72, 74 may be semi-tubular shaped and may be evenly spaced about the first surface 68 of the intermediate link 32 as shown in FIG. 4C. According to various embodiments, the first, second, and third grooves 70, 72, 74 may be configured in the shape of a segmented cylinder. The size of each of the grooves 70, 72, 74 may be identical to one another or may be different from one another. For example, according to various embodiments, the first and second grooves 70, 72 are configured as segments of a cylinder having a diameter on the order of approximately 1.75 millimeters at the first end 58 of the intermediate link 32, and the third groove 74 is configured as a segment of a cylinder having a diameter on the order of approximately 2.50 millimeters at the first end 58 of the intermediate link 32. The first, second and third grooves 70, 72, 74 are each configured to receive and partially surround any of a variety of tools or instruments (e.g., ablation tools) which may pass from the first end 24 of the multi-linked device 10 to the second end 26 of the multi-linked device 10.

The intermediate link 32 also defines a passage 76 extending from the first end 58 to the second end 60 along the longitudinal axis 62 as shown in FIG. 4B. The passage 76 may be of a size sufficient allow one or more cables 22 to pass therethrough. According to various embodiments, the passage 76 may be of a size sufficient to allow a tensioning cable to pass therethrough. According to various embodiments, the passage 76 is generally configured as a complex shape that comprises a combination of a first segmented hemisphere 78 that extends from the first end 58 toward the second end 60, a second segmented hemisphere 80 that extends from the first segmented hemisphere 78 toward the second end 60, a cylinder 82 that extends from the second segmented hemisphere 80 toward the second end 60, and a third segmented hemisphere 84 that extends from the cylinder 82 to the second end 60 of the intermediate link 32. According to various embodiments, the first segmented hemisphere 78 represents a portion of a sphere having a diameter on the order of approximately 4.75 millimeters, the second segmented hemisphere 80 represents a portion of a sphere having a diameter on the order of approximately 2.25 millimeters, the cylinder 82 may have a diameter on the order of approximately 1.0 millimeter, and the third segmented hemisphere 84 represents a portion of a sphere having a diameter on the order of approximately 2.25 millimeters. Other sizes are possible.

The first segmented hemisphere 78 of the passage 76 is configured to receive the second end 36 of the first link 28 when the first link 28 is coupled to the intermediate link 32. Similarly, for a given intermediate link 32, the first segmented hemisphere 78 of the passage 76 is configured to receive the second end 60 of another intermediate link 32 when the other intermediate link 32 is coupled to the given intermediate link 32. The third segmented hemisphere 84 may serve to reduce the pinching or binding a cable when one intermediate link 32 moves relative to an adjacent intermediate link 32 coupled thereto. Similarly, when the second link 30 is coupled to a given intermediate link 32, the third segmented hemisphere 84 may serve to reduce the pinching or binding of a cable when the second link 30 moves relative to the given intermediate link 32.

With the above described structure, the first link 28 may be coupled to the intermediate link 32 by seating the second end 36 of the first link 28 in the first segmented hemisphere 78 of the passage 76 of the intermediate link 32. As the convex configuration of the second end 36 of the first link 28 generally corresponds with the concave configuration of the first segmented hemisphere 78 of the passage 76 of the intermediate link 32, the first link 28 may be coupled to the intermediate link 32 such that the longitudinal axis 38 and the first, second and third grooves 46, 48, 50 of the first link 28 are respectively aligned with the longitudinal axis 62 and the first, second and third grooves 70, 72, 74 of the intermediate link 32. The intermediate link 32 may be moved relative to the first link 28 such that the longitudinal axis 62 of the intermediate link 32 is not aligned with the longitudinal axis 38 of the first link 28. According to various embodiments, the configuration of the first link 28 and the intermediate link 32 allows for the intermediate link 32 to be moved relative to the first link 28 coupled thereto such that the longitudinal axis 38 of the first link 28 and the longitudinal axis 62 of the intermediate link 32 are up to approximately 25° out of alignment with one another. Similarly, one intermediate link 32 may be coupled to another intermediate link 32, and so on, by seating the second end 60 of one intermediate link 32 in the first segmented hemisphere 78 of the passage 76 of another intermediate link 32. As the convex configuration of the second end 60 of the intermediate link 32 generally corresponds with the concave configuration of the first segmented hemisphere 78 of the passage 76 of the intermediate link 32, the intermediate links 32 may be coupled such that the respective longitudinal axes 62 and the respective first, second and third grooves 46, 48, 50 of the intermediate links 32 are aligned. The coupled intermediate links 32 may be moved relative to one another such that the respective longitudinal axes 62 of the coupled intermediate links 32 are not aligned. According to various embodiments, the configuration of the coupled intermediate links 32 allows for one intermediate link 32 to be moved relative to an adjacent intermediate link 32 coupled thereto such that the respective longitudinal axes 62 are up to approximately 25° out of alignment with one another.

Figure 5A:
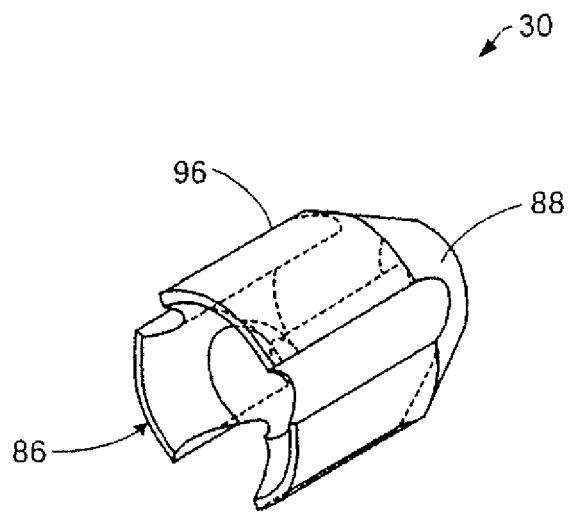
FIGS. 5A-5C illustrate various embodiments of a distal link of the core mechanism.
Figure 5B:
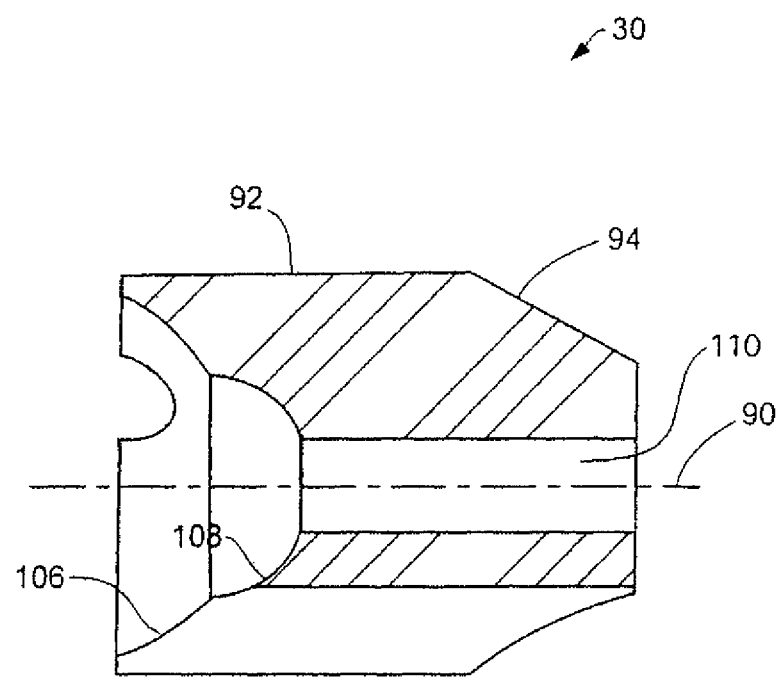
Figure 5C:
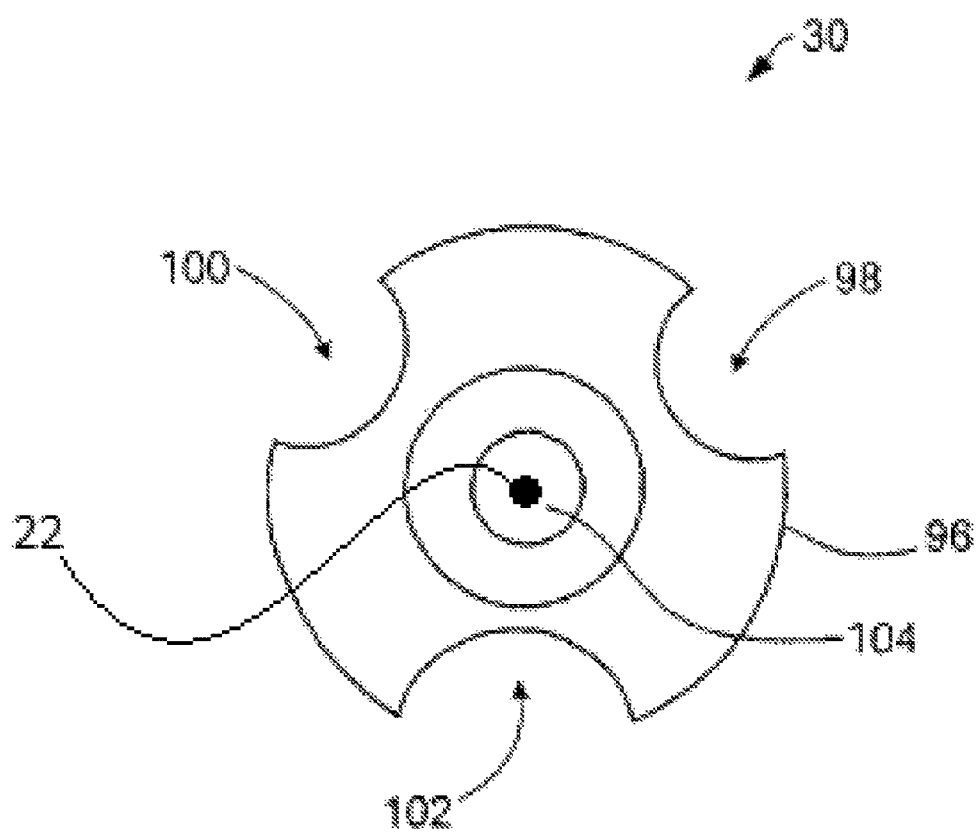

FIGS. 5A-5C illustrate various embodiments of the second link 30 (inner distal link) of the first mechanism 12. The second link 30 includes a first end 86 and a second end 88, and defines a longitudinal axis 90 that passes through the center of the first end 86 and the center of the second end 88 as shown in FIG. 5B. The second link 30 may be fabricated from any suitable material. According to various embodiments, the second link 30 is fabricated from a thermoplastic material such as, for example, Delrin®.

The second link 30 comprises a first portion 92 and a second portion 94. The first portion 92 may be considered the proximal portion and the second portion 94 may be considered the distal portion. The first portion 92 may be fabricated integral with the second portion 94. The first portion 92 has a generally cylindrical shaped exterior, and extends from the first end 86 of the second link 30 toward the second end 88 of the second link 30. According to various embodiments, the second portion 94 has a generally cylindrically shaped exterior where it contacts the first portion 92, and tapers toward the second end 88 of the second link 30. The exterior of the second portion 64 is configured in the form of a generally segmented cone. According to various embodiments, the diameter of the second link 30 may be on the order of approximately 4.75 millimeters at the first end 86 thereof, and the taper of the second portion 94 may be at an angle of approximately 30° relative to the exterior of the first portion 92. The length of the second link 30 may be on the order of approximately 5.90 millimeters. However, one skilled in the art will appreciate that the length or diameter of the second link 30 can vary based on the application.

The second link 30 also comprises a first surface 96 that extends from the first end 86 of the second link 30 to the second end 88 of the second link 30. The first surface 96 may be considered the outer surface of the second link 30. The second link 30 also defines a first groove 98 parallel to the longitudinal axis 90 along the first surface 96, a second groove 100 parallel to the longitudinal axis 90 along the first surface 96, and a third groove 102 parallel to the longitudinal axis 90 along the first surface 96. Each of the first, second and third grooves 98, 100, 102 extend along the first surface 96 from the first end 86 of the second link 30 toward the second end 88 of the second link 30. The first, second and third grooves 98, 100, 102 may be semi-tubular shaped and may be evenly spaced about the first surface 96 of the second link 30 as shown in FIG. 5C. According to various embodiments, the first, second, and third grooves 98, 100, 102 may be configured in the shape of a segmented cylinder. The size of each of the grooves 98, 100, 102 may be identical to one another or may be different from one another. For example, according to various embodiments, the first and second grooves 98, 100 are configured as segments of a cylinder having a diameter on the order of approximately 1.25 millimeters at the first end 86 of the second link 30, and the third groove 102 is configured as a segment of a cylinder having a diameter on the order of approximately 2.50 millimeters at the first end 86 of the second link 30. The first, second and third grooves 98, 100, 102 are each configured to receive and partially surround any of a variety of tools or instruments (e.g., ablation tools) which may pass from the first end 24 of the multi-linked device 10 to the second end 26 of the multi-linked device 10.

The second link 30 also defines a passage 104 extending from the first end 86 to the second end 88 along the longitudinal axis 90 as shown in FIG. 5B. The passage 104 may be of a size sufficient to allow at least one cable 22 to pass therethrough. According to various embodiments, the passage 104 may be of a size sufficient to allow a tensioning cable to pass therethrough. According to various embodiments, the passage 104 is generally configured as a complex shape that comprises a combination of a first segmented hemisphere 106 that extends from the first end 86 toward the second end 88, a second segmented hemisphere 108 that extends from the first segmented hemisphere 106 toward the second end 88, and a cylinder 110 that extends from the second segmented hemisphere 108 to the second end 88 of the second link 30. According to various embodiments, the first segmented hemisphere 106 represents a portion of a sphere having a diameter on the order of approximately 4.75 millimeters, the second segmented hemisphere 108 represents a portion of a sphere having a diameter on the order of approximately 2.50 millimeters, and the cylinder 110 may have a diameter on the order of approximately 1.0 millimeter. The first segmented hemisphere 106 of the passage 104 may be configured to receive the second end 60 of an intermediate link 32 when the intermediate link 32 is coupled to the second link 30.

With the above described structure, an intermediate link 32 may be coupled to the second link 30 by seating the second end 60 of the intermediate link 32 in the first segmented hemisphere 106 of the passage 104 of the second link 30. As the convex configuration of the second end 60 of the intermediate link 32 generally corresponds with the concave configuration of the first segmented hemisphere 106 of the passage 104 of the second link 30, the intermediate link 32 may be coupled to the second link 30 such that the longitudinal axis 62 and the first, second and third grooves 70, 72, 74 of the intermediate link 32 are respectively aligned with the longitudinal axis 90 and the first, second and third grooves 98, 100, 102 of the second link 30. The second link 30 may be moved relative to the intermediate link 32 coupled thereto such that the respective longitudinal axes 62, 90 are not aligned. According to various embodiments, the configuration of the second link 30 allows for an intermediate link 32 coupled thereto to be moved relative to the second link 30 such that the respective longitudinal axes 62, 90 are up to approximately 25° out of alignment with one another.

Figure 6:
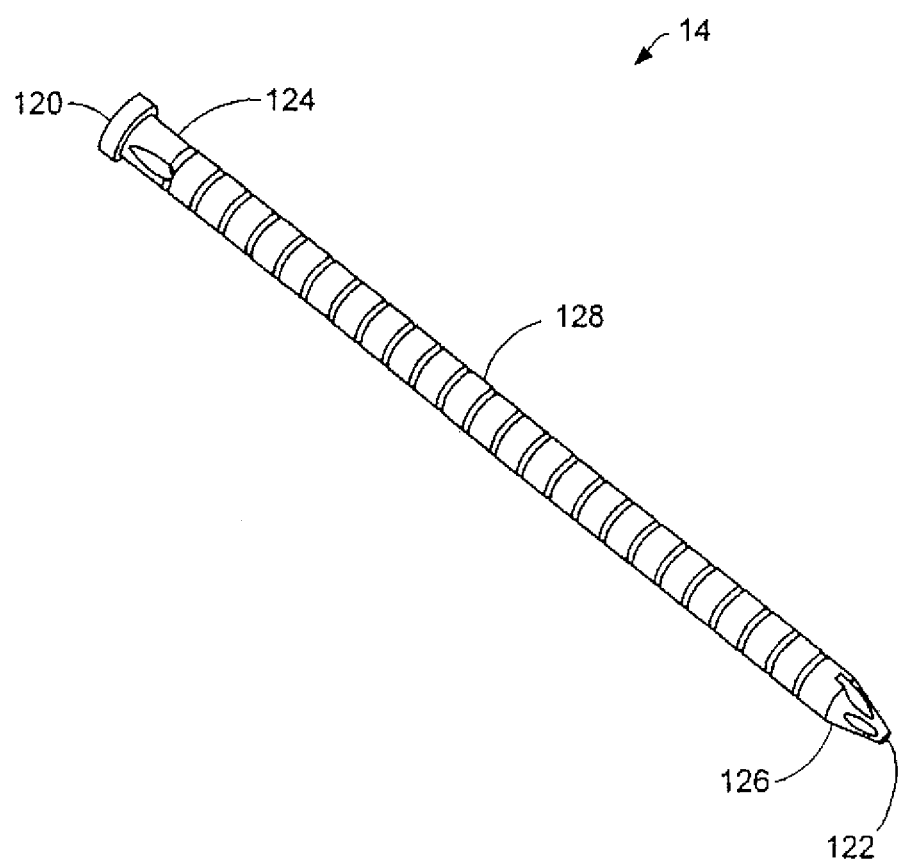
FIG. 6 illustrates various embodiments of a sleeve mechanism of the device of FIG. 1.

FIG. 6 illustrates various embodiments of the second mechanism 14 of the device 10. The second mechanism 14 is a multi-linked mechanism and includes a first end 120 and a second end 122. The first end 120 may be considered the proximal end and the second end 122 may be considered the distal end. The second mechanism 14 comprises a first link 124, a second link 126, and any number of intermediate links 128 between the first and second links 124, 126. The first link 124 may be considered the proximal link, and the second link 126 may be considered the distal link.

Figure 7A:
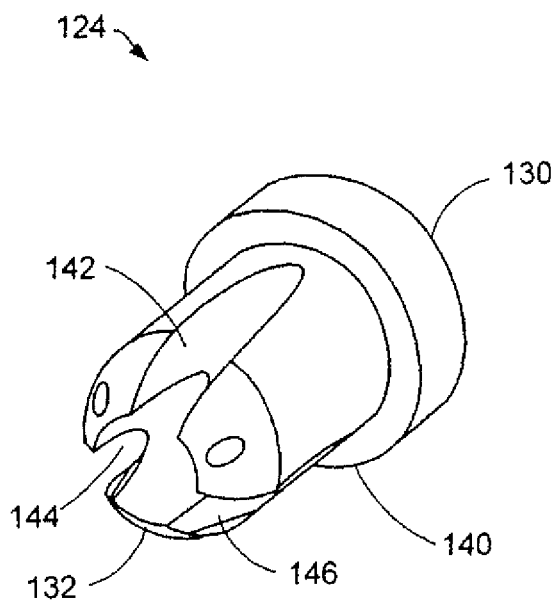
FIGS. 7A-7C illustrate various embodiments of a proximal link of the sleeve mechanism.
Figure 7B:
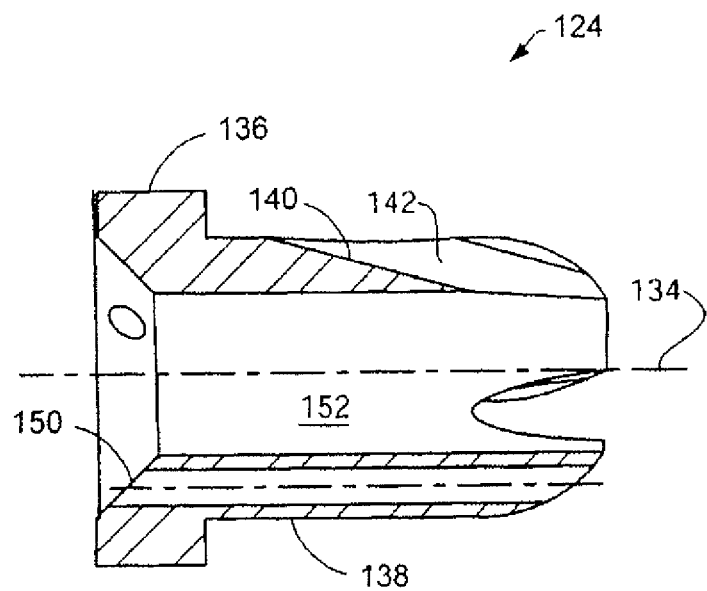
Figure 7C:
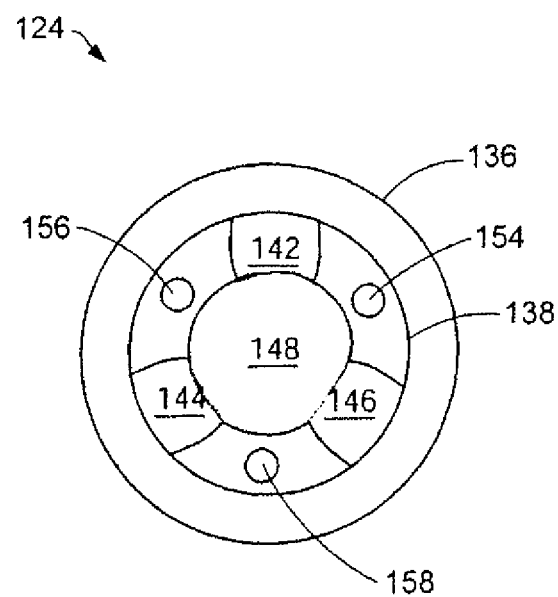

FIGS. 7A-7C illustrate various embodiments of the first link 124 (outer proximal link) of the second mechanism 14. The first link 124 includes a first end 130 and a second end 132, and defines a longitudinal axis 134 that passes through the center of the first end 130 and the center of the second end 132 as shown in FIG. 7B. The first link 124 may be fabricated from any suitable material. According to various embodiments, the first link 124 is fabricated from a stainless steel material such as, for example, 316 stainless steel. The first link 124 has a generally bullet-shaped exterior and is described in more detail hereinbelow.

The first link 124 comprises a first portion 136 and a second portion 138. The first portion 136 may be considered the proximal portion and the second portion 138 may be considered the distal portion. The first portion 136 may be fabricated integral with the second portion 138. The first portion 136 has a cylindrical shaped exterior, and extends from the first end 130 of the first link 124 toward the second end 132 of the first link 124. According to various embodiments, the diameter of the first portion 136 may be on the order of approximately 12.70 millimeters. Other sizes are possible.

The second portion 138 has a generally cylindrically shaped exterior. The second portion 138 has a cylindrically shaped exterior where it contacts the first portion 136, and tapers toward the second end 132 of the first link 124. The second portion 138 may be shaped in the form of a generally segmented hemisphere at the second end 132 of the first link 124. According to various embodiments, the diameter of the second portion 138 may be on the order of approximately 9.50 millimeters where it contacts the first portion 136. Other sizes and shapes are possible.

The second portion 138 comprises a first surface 140. The first surface 140 may be considered the outer surface of the second portion 138. The second portion 138 defines a first groove 142 along the first surface 140, a second groove 144 along the first surface 140, and a third groove 146 along the first surface 140. Each of the first, second and third grooves 142, 144, 146 are oblique relative to the longitudinal axis 134 and extend along the first surface 140 toward the second end 132 of the first link 124. According to various embodiments, each of the grooves 142, 144, 146 are oriented at an angle on the order of approximately 15° relative to the longitudinal axis 134. As shown in FIG. 7C, the first, second and third grooves 142, 144, 146 may be evenly spaced about the first surface 140 of the first link 124. According to various embodiments, the first, second, and third grooves 142, 144, 146 may be configured in the shape of a segmented cylinder. The size of each of the grooves 142, 144, 146 may identical to one another or may be different from one another. For example, according to various embodiments, each of the grooves 142, 144, 146 are configured as segments of respective cylinders having diameters on the order of approximately 3.0 millimeters. The first, second and third grooves 142, 144, 146 are each configured to facilitate the introduction of various tools or instruments (e.g., ablation tools) into the multi-linked device 10. The length of the first link 124 may be on the order of approximately 18.5 millimeters. However, one skilled in the art will appreciate that the length or diameter of the first link 124 can vary based on the application.

The first link 124 also defines a passage 148 extending from the first end 130 to the second end 132 along the longitudinal axis 134 as shown in FIG. 7B. The passage 148 is of a size sufficient to allow the first mechanism 12 to pass therethrough. According to various embodiments, the passage 148 is generally configured as a complex shape that comprises a combination of a segmented cone 150 that extends from the first end 130 toward the second end 132, and a cylinder 152 that extends from the segmented cone 150 to the second end 132 of the first link 124. According to various embodiments, the segmented cone 150 has a diameter on the order of approximately 7.0 millimeters at the first end 130 of the first link 124, and may be tapered at an angle on the order of approximately 45° relative to the longitudinal axis 134. The cylinder 152 may have a diameter on the order of approximately 5.50 millimeters. Other dimensions are possible.

The first link 124 also defines a first through-hole 154, a second through-hole 156, and a third through-hole 158. (See FIG. 7C). The first through-hole 154 is substantially parallel to the longitudinal axis 134, extends from the first portion 136 toward the second end 132, and is positioned between the passage 148 and the first surface 140. The second through-hole 156 is substantially parallel to the longitudinal axis 134, extends from the first portion 136 to the second end 132, and is positioned between the passage 148 and the first surface 140. The third through-hole 158 is substantially parallel to the longitudinal axis 134, extends from the first portion 136 to the second end 132, and is positioned between the passage 148 and the first surface 140. The first, second and third through-holes 154, 156, 158 are generally cylindrically shaped. According to various embodiments, the through-holes 154, 156, 158 are evenly spaced from one another as shown in FIG. 7C. The size of each of the through-holes 154, 156, 158 may be identical to one another or may be different from one another. For example, according to various embodiments, the respective diameters associated with the through-holes 154, 156, 158 may each be on the order of approximately 1.20 millimeters. The first through-hole 154 is configured to receive and surround a cable. The second through-hole 156 is configured to receive and surround a cable. The third through-hole 158 is configured to receive and surround a cable. The first, second and third through-holes 154, 156, 158 may serve as guidepaths for movement of the cables.

Figure 8A:
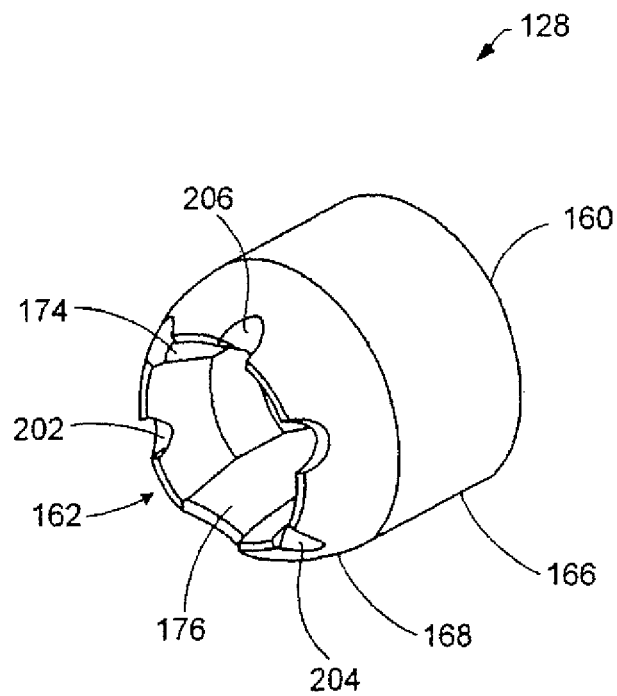
FIGS. 8A-8C illustrate various embodiments of an intermediate link of the sleeve mechanism.
Figure 8B:
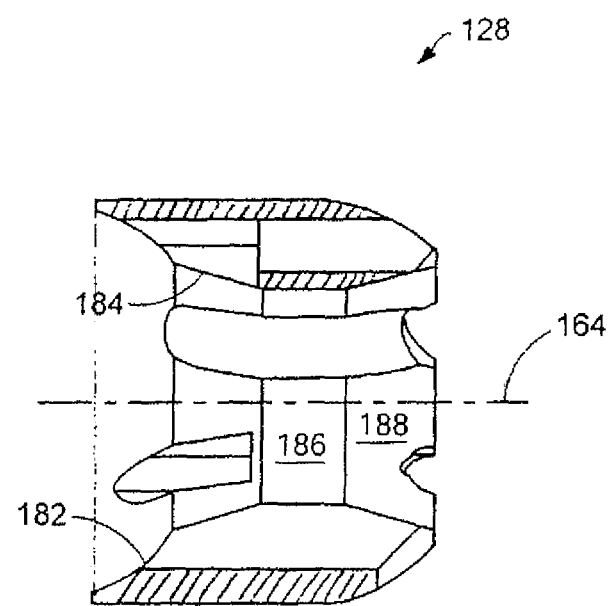
Figure 8C:
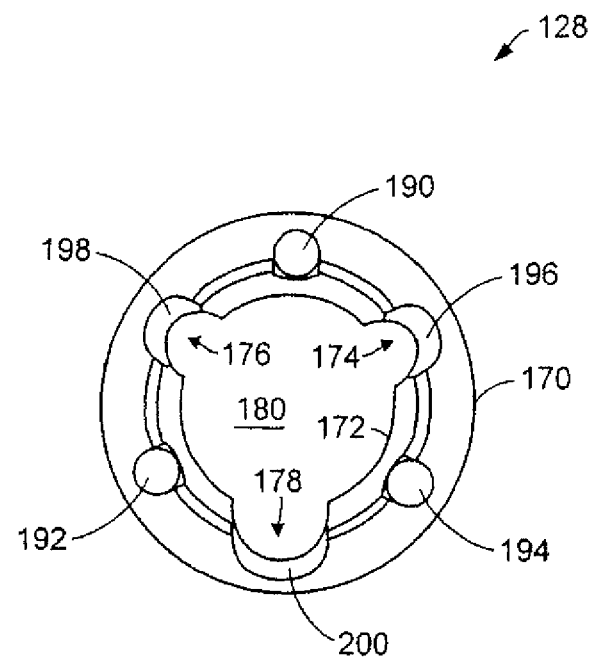

FIGS. 8A-8C illustrate various embodiments of one of the intermediate links 128 (outer intermediate link) of the second mechanism 14. The intermediate link 128 is representative of the other intermediate links 128. The intermediate link 128 includes a first end 160 and a second end 162, and defines a longitudinal axis 164 that passes through the center of the first end 160 and the center of the second end 162 as shown in FIG. 8C. The intermediate link 128 may be fabricated from any suitable material. According to various embodiments, the intermediate link 128 is fabricated from a polymer thermosplastic material such as, for example, polysulfone. The intermediate link 128 has a generally bullet-shaped exterior and is described in more detail hereinbelow.

The intermediate link 128 comprises a first portion 166 and a second portion 168. The first portion 166 may be considered the proximal portion and the second portion 168 may be considered the distal portion. The first portion 166 may be fabricated integral with the second portion 168. The first portion 166 has a generally cylindrical shaped exterior, and extends from the first end 160 of the intermediate link 128 toward the second end 162 of the intermediate link 128. According to various embodiments, the second portion 168 has a generally cylindrically shaped exterior where it contacts the first portion 166, and tapers toward the second end 162 of the intermediate link 128. The exterior of the second portion 168 is configured in the form of a generally segmented hemisphere. According to various embodiments, the diameter of the intermediate link 128 is on the order of approximately 9.65 millimeters at the first end 160 thereof. The length of the intermediate link 128 may be on the order of approximately 8.40 millimeters. However, one skilled in the art will appreciate that the dimensions of the intermediate link 128 can vary based on the application.

The intermediate link 128 also comprises a first surface 170 that extends from the first end 160 of the intermediate link 128 to the second end 162 of the intermediate link 128, and a second surface 170 that extends from the first end 160 of the intermediate link 128 to the second end 162 of the intermediate link 128. The first surface 170 may be considered the outer surface of the intermediate link 128, and the second surface 172 may be considered the inner surface of the intermediate link 128. The intermediate link 32 also defines a first groove 174 substantially parallel to the longitudinal axis 164 along the second surface 172, a second groove 176 substantially parallel to the longitudinal axis 164 along the second surface 172, and a third groove 178 substantially parallel to the longitudinal axis 164 along the second surface 172. Each of the first, second and third grooves 174, 176, 178 extend along the second surface 172 toward the second end 162 of the intermediate link 128. The first, second and third grooves 174, 176, 178 may be semi-tubular shaped and may be evenly spaced about the second surface 172 of the intermediate link 128 as shown in FIG. 8C. According to various embodiments, the first, second, and third grooves 174, 176, 178 may be configured in the shape of a segmented cylinder. The size of each of the grooves 174, 176, 178 may be identical to one another or may be different from one another. For example, according to various embodiments, the first and second grooves 174, 176 are configured as segments of cylinders having diameters on the order of approximately 1.75 millimeters at the first end 160 of the intermediate link 128, and the third groove 178 is configured as a segment of a cylinder having a diameter on the order of approximately 2.50 millimeters at the first end 160 of the intermediate link 128. The first, second and third grooves 174, 176, 178 are each configured to receive and partially surround any of a variety of tools or instruments (e.g., ablation tools) which may pass from the first end 24 of the multi-linked device 10 to the second end 26 of the multi-linked device 10.

The intermediate link 128 also defines a passage 180 extending from the first end 160 to the second end 162 along the longitudinal axis 164 as shown in FIG. 8B. The passage 180 is of a size sufficient to allow the first mechanism 12 to pass therethrough. According to various embodiments, the passage 180 is generally configured as a complex shape that comprises a combination of a segmented hemisphere 182 that extends from the first end 160 toward the second end 162, a first segmented cone 184 that extends from the segmented hemisphere 182 toward the second end 162, a cylinder 186 that extends from the first segmented cone 184 toward the second end 162, and a second segmented cone 188 that extends from the cylinder 186 to the second end 162 of the intermediate link 128. According to various embodiments, the segmented hemisphere 182 represents a portion of a sphere having a diameter on the order of approximately 9.65 millimeters, the first segmented cone 184 is tapered at an angle on the order of approximately 15° relative to the longitudinal axis 164, the cylinder 186 has a diameter on the order of approximately 5.50 millimeters, and the second segmented cone 188 is tapered at an angle on the order of approximately 15° relative to the longitudinal axis 164. The segmented hemisphere 182 of the passage 180 is configured to receive the second end 132 of the first link 124 when the first link 124 is coupled to the intermediate link 128. Similarly, for a given intermediate link 128, the segmented hemisphere 182 of the passage 180 is configured to receive the second end 162 of another intermediate link 128 when the other intermediate link 128 is coupled to the given intermediate link 128.

The intermediate link 128 also defines a first through-hole 190, a second through-hole 192, and a third through-hole 194. (See FIG. 8C). The first through-hole 190 is substantially parallel to the longitudinal axis 164, extends from the first portion 166 toward the second end 162, and is positioned between the passage 180 and the first surface 170. The second through-hole 192 is substantially parallel to the longitudinal axis 164, extends from the first portion 166 to the second end 162, and is positioned between the passage 180 and the first surface 170. The third through-hole 194 is substantially parallel to the longitudinal axis 164, extends from the first portion 166 to the second end 162, and is positioned between the passage 180 and the first surface 170. The first, second and third through-holes 190, 192, 194 are generally cylindrically shaped. According to various embodiments, the through-holes 190, 192, 194 are evenly spaced from one another. The size of each of the through-holes 190, 192, 194 may be identical to one another or may be different from one another. For example, according to various embodiments, the respective diameters associated with the through-holes 190, 192, 194 may each be on the order of approximately 1.25 millimeters. The first through-hole 190 is configured to receive and surround a cable. The second through-hole 192 is configured to receive and surround a cable. The third through-hole 194 is configured to receive and surround a cable. The first, second and third through-holes 190, 192, 194 may serve as guidepaths for movement of the cables.

As shown in FIG. 8C, the intermediate link 128 also defines first, second and third indents 196, 198, 200 at the second end 162 thereof resulting, in part, from the combination of the taper associated with the second portion 168 and the configuration and orientation of the first, second, and third grooves 174, 176, 178. The first, second and third indents 196, 198, 200 may be evenly spaced about the second end 162 of the intermediate link 128 as shown in FIG. 8C. The first, second and third indents 196, 198, 200 may serve to reduce the pinching or binding of various tools or instruments (e.g., ablation tools) when one intermediate link 128 of the second mechanism 14 is moved relative to another intermediate link 128 coupled thereto.

The intermediate link 128 also defines fourth, fifth and sixth indents 202, 204, 206 at the second end 162 thereof resulting from the combination of the taper associated with the second portion 168 and the configuration and orientation of the first, second, and third through-holes 190, 192, 194. The fourth, fifth and sixth indents 202, 204, 206 may be evenly spaced about the second end 162 of the intermediate link 128, and may be evenly spaced from the first, second and third indents 196, 198, 200 as shown in FIG. 8C. The fourth, fifth and sixth indents 202, 204, 206 may serve to reduce the pinching or binding of the cables when one intermediate link 128 of the second mechanism 14 is moved relative to another intermediate link 128 coupled thereto.

According to various embodiments, an intermediate link 128 may also define an opening (not shown) that extends from the second surface 172 or from one of the grooves 174, 176, 178 to the first surface 170 of the intermediate link 128. The intermediate link 128 may have any number of such openings, and any number of the intermediate links 128 may have such openings. Referring to FIGS. 2 and 4, the opening may be utilized as an exit point for a tool or instrument which may pass from the first end 24 of the multi-linked device 10 toward the second end 26 of the multi-linked device 10. For such embodiments, the respective intermediate link 128 may be positioned proximate to the second link 126 of the second mechanism 14. The opening may be oriented at any angle relative to the longitudinal axis 134 of the intermediate link 128. When the first mechanism 12 is removed from the second mechanism 14, and a relatively large tool or instrument is advanced from the first end 120 of the second mechanism 14 to the second end 122 of the second mechanism 14, sufficient room may not exist for a second tool or instrument (e.g., fiber optic cable) to pass through the second end 122 of the second mechanism 14. For such instances, the second tool or instrument may exit through an opening of one of the intermediate links 128.

With the above described structure, the first link 124 may be coupled to the intermediate link 128 by seating the second end 132 of the first link 124 in the segmented hemisphere 182 of the passage 180 of the intermediate link 128. As the convex configuration of the second end 132 of the first link 124 generally corresponds with the concave configuration of the segmented hemisphere 182 of the passage 180 of the intermediate link 128, the first link 124 may be coupled to the intermediate link 128 such that the longitudinal axis 134, the first, second and third grooves 142, 144, 146, and the first, second and third through-holes 154, 156, 158 of the first link 124 are respectively aligned with the longitudinal axis 164, the first, second and third grooves 174, 176, 178, and the first, second and third through-holes 190, 192, 194 of the intermediate link 128. The intermediate link 128 may be moved relative to the first link 124 such that the longitudinal axis 164 of the intermediate link 128 is not aligned with the longitudinal axis 134 of the first link 124. According to various embodiments, the configuration of the first link 124 and the intermediate link 128 allows for the intermediate link 128 to be moved relative to the first link 124 coupled thereto such that the longitudinal axis 134 of the first link 124 and the longitudinal axis 164 of the intermediate link 128 are up to approximately 10° out of alignment with one another. Similarly, one intermediate link 128 may be coupled to another intermediate link 128, and so on, by seating the second end 162 of one intermediate link 128 in the segmented hemisphere 182 of the passage 180 of another intermediate link 128. As the convex configuration of the second end 162 of the intermediate link 128 generally corresponds with the concave configuration of the segmented hemisphere 182 of the passage 180 of the intermediate link 128, the intermediate links 128 may be coupled such that the respective longitudinal axes 164, the respective first, second and third grooves 174, 176, 178, and the respective first, second and third through-holes 190, 192, 194 of the intermediate links 128 are aligned. The coupled intermediate links 128 may be moved relative to one another such that the respective longitudinal axes 164 of the coupled intermediate links 128 are not aligned. According to various embodiments, the configuration of the coupled intermediate links 128 allows for one intermediate link 128 to be moved relative to another intermediate link 128 coupled thereto such that the respective longitudinal axes 164 are up to approximately 10° out of alignment with one another.

Figure 9A:
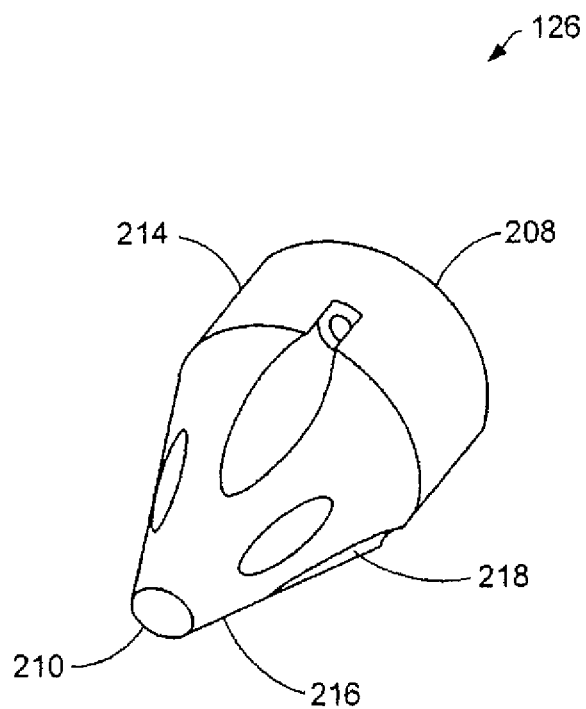
FIGS. 9A-9D illustrate various embodiments of a distal link of the sleeve mechanism.
Figure 9B:
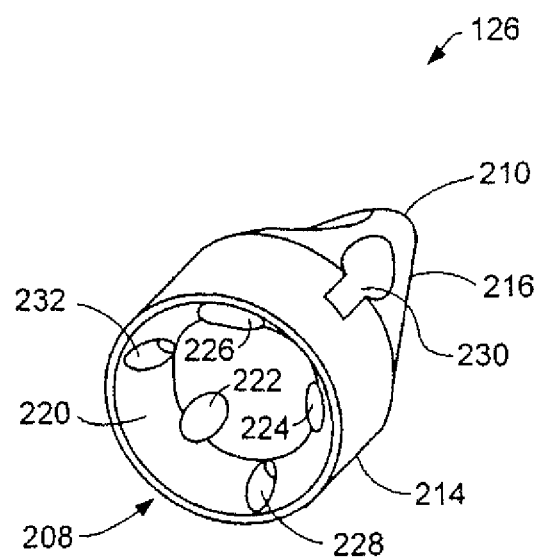
Figure 9C:
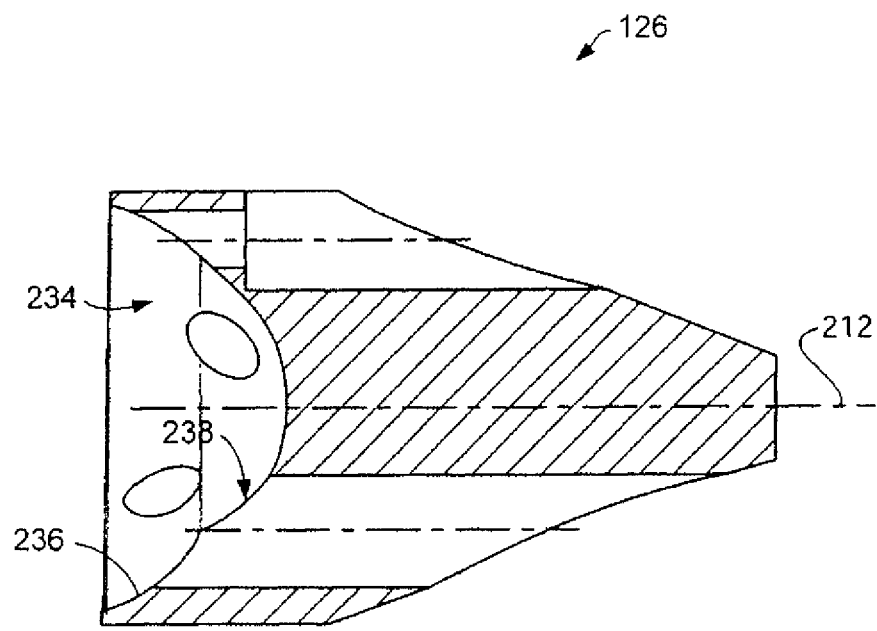

FIGS. 9A-9D illustrate various embodiments of the second link 126 (outer distal link) of the second mechanism 14. The second link 126 includes a first end 208 and a second end 210, and defines a longitudinal axis 212 that passes through the center of the first end 208 and the center of the second end 210 as shown in FIG. 9C. The second link 126 may be fabricated from any suitable material. According to various embodiments, the second link 126 is fabricated from a thermoplastic material such as, for example, Delrin®.

The second link 126 comprises a first portion 214 and a second portion 216. The first portion 214 may be considered the proximal portion and the second portion 216 may be considered the distal portion. The first portion 214 may be fabricated integral with the second portion 216. The first portion 214 has a generally cylindrical shaped exterior, and extends from the first end 208 of the second link 126 toward the second end 210 of the second link 126. According to various embodiments, the diameter of the first portion 214 is on the order of approximately 4.80 millimeters.

According to various embodiments, the second portion 216 has a generally cylindrically shaped exterior where it contacts the first portion 214, and tapers toward the second end 210 of the second link 126. The exterior of the second portion 216 is configured in the form of a generally segmented cone. According to various embodiments, the exterior of the second portion 216 tapers from the first portion 214 to the second end 210 of the second link 126 at an angle on the order of approximately 20° relative to the exterior of the first portion 214. The length of the second link 126 may be on the order of approximately 15 millimeters. However, one skilled in the art will appreciate that the length of the second link 126 can vary based on the application.

The second link 126 also comprises a first surface 218 that extends from the first end 208 of the second link 126 to the second end 210 of the second link 126, and a second surface 220 that extends from the first end 208 of the second link 126 toward the second end 210 of the second link 126. The first surface 218 may be considered the outer surface of the second link 126, and the second surface 220 may be considered the inner surface of the second link 126.

Figure 9D:
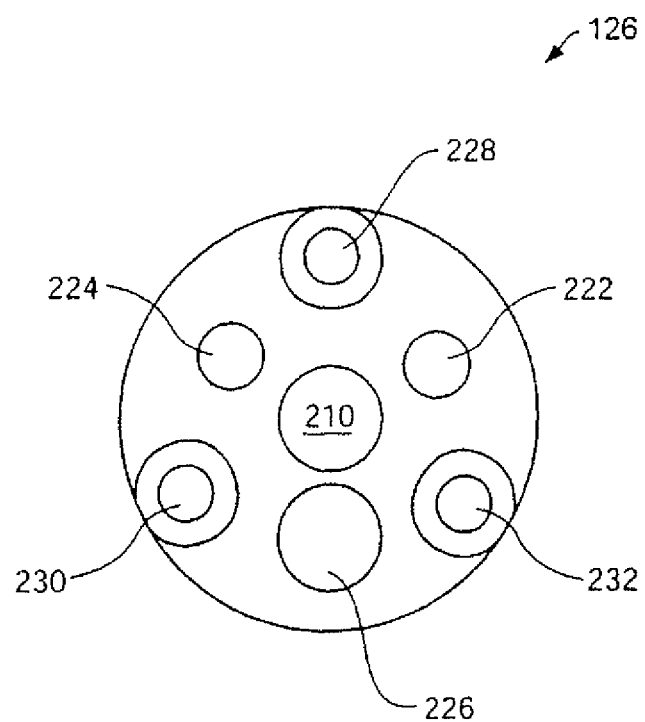

The second link 126 also defines a first port 222, a second port 224, and a third port 226. (See FIG. 9B). The first port 222 extends from the second surface 220 to the first surface 218 and is substantially parallel to the longitudinal axis 212. The second port 224 extends from the second surface 220 to the first surface 218 and is substantially parallel to the longitudinal axis 212. The third port 226 extends from the second surface 220 to the first surface 218 and is substantially parallel to the longitudinal axis 212. The first, second and third ports 222, 224, 226 may be cylindrical shaped and may be evenly spaced about the longitudinal axis 212 of the second link 126 as shown in FIG. 9D. The size of each of the ports 222, 224, 226 may be identical to one another or may be different from one another. For example, according to various embodiments, the first and second ports 222, 224 are configured as cylinders having diameters on the order of approximately 1.50 millimeters, and the third port 226 is configured as a cylinder having a diameter on the order of approximately 2.50 millimeters. Other dimensions are possible. The first, second and third ports 222, 224, 226 are each configured to receive and surround any of a variety of tools or instruments (e.g., ablation tools) which may pass from the first end 24 of the multi-linked device 10 to the second end 26 of the multi-linked device 10.

The second link 126 also defines a first through-hole 228, a second through-hole 230, and a third through-hole 232. (See FIG. 9B). The first through-hole 228 extends from the second surface 220 to the first surface 218 and is substantially parallel to the longitudinal axis 212. The second through-hole 230 extends from the second surface 220 to the first surface 218 and is substantially parallel to the longitudinal axis 212. The third through-hole 232 extends from the second surface 220 to the first surface 218 and is substantially parallel to the longitudinal axis 212. The first, second and third through-holes 228, 230, 232 are generally cylindrically shaped. According to various embodiments, the through-holes 228, 230, 232 are evenly spaced from one another as shown in FIG. 9D. The size of each of the through-holes 228, 230, 232 may be identical to one another or may be different from one another. For example, according to various embodiments, the respective diameters associated with the through-holes 228, 230, 232 may each be on the order of approximately 1.25 millimeters. The first through-hole 228 is configured to receive and surround a cable. The second through-hole 230 is configured to receive and surround a cable. The third through-hole 232 is configured to receive and surround a cable.

The second link 126 also defines a recess 234 that extends from the first end 208 toward the second end 210 along the longitudinal axis 212 as shown in FIG. 9C. According to various embodiments, the recess 234 is generally configured as a complex shape that comprises a combination of a first segmented hemisphere 236 that extends from the first end 208 toward the second end 210, and a second segmented hemisphere 238 that extends from the first segmented hemisphere 236 toward the second end 210 of the second link 126. According to various embodiments, the first segmented hemisphere 236 represents a portion of a sphere having a diameter on the order of approximately 9.50 millimeters, and the second segmented hemisphere 238 represents a portion of a sphere having a diameter on the order of approximately 7.0 millimeters. The first segmented hemisphere 236 of the recess 234 is configured to receive the second end 162 of an intermediate link 128 when the intermediate link 128 is coupled to the second link 126.

With the above described structure, an intermediate link 128 may be coupled to the second link 126 by seating the second end 162 of the intermediate link 128 in the first segmented hemisphere 236 of the recess 234 of the second link 126. As the convex configuration of the second end 162 of the intermediate link 128 generally corresponds with the concave configuration of the first segmented hemisphere 236 of the recess 234 of the second link 126, the intermediate link 128 may be coupled to the second link 126 such that the longitudinal axis 164, the first, second and third grooves 174, 176, 178, and the first, second and third through-holes 190, 192, 194 of the intermediate link 128 are respectively aligned with the longitudinal axis 212, the first, second and third ports 222, 224, 226, and the first, second and third through-holes 228, 230, 232 of the second link 126. The second link 126 may be moved relative to the intermediate link 128 coupled thereto such that the respective longitudinal axes 164, 212 are not aligned. According to various embodiments, the configuration of the second link 126 allows for an intermediate link 128 coupled thereto to be moved relative to the second link 126 such that the respective longitudinal axes 164, 212 are up to approximately 10° out of alignment with one another.

When the first mechanism 12 is inserted into the second mechanism 14, the first second and third grooves 70, 72, 74 of the intermediate links 32 of the first mechanism 12 may be substantially aligned with the first, second and third grooves 174, 176, 178 of the intermediate links 128 of the second mechanism 14, and the first, second and third grooves 98, 100, 102 of the second link 30 of the first mechanism 12 may be substantially aligned with the first, second and third ports 222, 224, 226 of the second link 126 of the second mechanism 14. The combination of the first grooves 70 of the intermediate links 32 of the first mechanism 12 aligned with the first grooves 174 of the intermediate links 128 of the second mechanism 14 allows the respective first grooves 70, 174 to collectively serve as a first working port that is substantially aligned with the first port 222 of the second link 126 of the second mechanism 14. The first groove 70 may be considered the inner portion of the first working port and the first groove 174 may be considered the outer portion of the first working port.

Similarly, the combination of the second grooves 72 of the intermediate links 32 of the first mechanism 12 aligned with the second grooves 176 of the intermediate links 128 of the second mechanism 14 allows the respective second grooves 72, 176 to collectively serve as a second working port that is substantially aligned with the second port 224 of the second link 126 of the second mechanism 14, and the combination of the third grooves 74 of the intermediate links 32 of the first mechanism 12 aligned with the third grooves 178 of the intermediate links 128 of the second mechanism 14 allows the respective third grooves 74, 178 to collectively serve as a third working port that is substantially aligned with the third port 226 of the second link 126 of the second mechanism 14. The second groove 72 may be considered the inner portion of the second working port and the second groove 176 may be considered the outer portion of the second working port. The third groove 74 may be considered the inner portion of the third working port and the third groove 178 may be considered the outer portion of the third working port. The first, second and third working ports may be utilized to pass various tools or instruments (e.g., ablation tools) from the first end 24 of the multi-linked device 10 to the second end 26 of the multi-linked device 10. For the exemplary sizes described hereinabove, the third working port is larger than the first and second working ports. Accordingly, the third working port may be utilized to carry a particular tool or instrument that is too large to be carried by the first or second working ports.

When the respective grooves 70, 72, 74, 174, 176, 178 of the respective intermediate links 32, 128 are aligned and collectively surround the various tools and instruments, the combination of the grooves 70, 72, 74, 174, 176, 178 and the tools and instruments may serve to limit or prevent the rotation of the first mechanism 12 relative to the second mechanism 14.

As the diameter of the passage 180 of the intermediate link 128 of the second mechanism 14 is larger than the diameter of any portion of the first mechanism 12, a three-dimensional space 240 exists between the first mechanism 12 and the second mechanism 14 when the first mechanism 12 is received by the second mechanism 14 (See FIG. 1B). According to various embodiments, the space 240 may be utilized to carry wiring, tools, instruments, etc. from the first end 24 of the multi-linked device 10 toward the second end 26 of the multi-linked device 10.

According to various embodiments, one or more steering cables may be fabricated from any suitable material. For example, according to various embodiments, the steering cables may be fabricated from a polyethylene fiber cable such as, for example, Spectra®. The steering cables may be utilized to control the movement of the multi-linked device 10. For example, by applying a substantially equal tension to each of the steering cables, the first mechanism 12 and/or second mechanism 14 may be steered in a direction such that the respective longitudinal axes 38, 62, 90, 134, 164, 212 of each of the links 28, 30, 32, 124, 126, 128 are all aligned. By applying a different tension to one or more of the steering cables, the first mechanism 12 and/or the second mechanism 14 may be steered in a direction such that the respective longitudinal axes 38, 62, 90, 134, 164, 212 of each of the links 28, 30, 32, 124, 126, 128 are not all aligned. The cables 16, 18, 20 may also be utilized to control the relative state of the second mechanism 14. For example, when a uniform tension is applied to the steering cables, the second mechanism 14 may be placed in a "rigid" state, and when a tension is removed from the steering cables, the second mechanism 14 may be placed in a "limp" state. According to various embodiments, one or more of the steering cables may be attached at the first end 130 of the first link 124 of the second mechanism 14 to respective pullies (not shown) by, for example, respective stopper knots. The steering cables may be attached to the second end 132 of the second link 126 of the second mechanism 14 by, for example, respective stopper knots. One skilled in the art will appreciate that, according to other embodiments, the "rigid" and "limp" states may be achieved by subjecting the first and/or second mechanisms 12, 14 to a twisting force, or by any other manner known in the art.

According to various embodiments, one or more tensioning cables may be fabricated from any suitable material. For example, according to various embodiments, the tensioning cables may be fabricated from a polyethylene fiber cable such as, for example, Spectra®. The tensioning cables may be utilized to control the relative state of the first mechanism 12. For example, when the tensioning cable is drawn tight, the first mechanism 12 may be placed in a "rigid" state, whereas when the tensioning cable is let loose, the first mechanism 12 may be placed in a "limp" state. According to various embodiments, the tensioning cable may be attached at the first end 34 of the first link 28 of the first mechanism 12 to a pully (not shown) by, for example, a stopper knot. The tensioning cable may be attached to the second end 88 of the second link 30 of the first mechanism 12 by, for example, a stopper knot.

Figure 10:
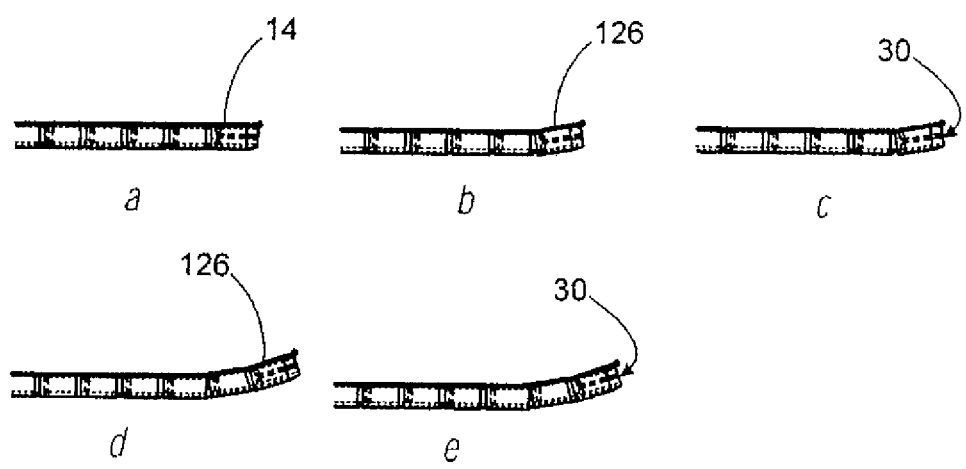
FIG. 10 illustrates various embodiments of a motion sequence of the device of FIG. 1.

FIG. 10 illustrates various embodiments of a motion sequence of the steerable multi-linked device 10. At the start of the sequence, the second mechanism 14 surrounds the first mechanism 12 as shown in step "a" of FIG. 10, the longitudinal axes 38, 62, 90 of the links 28, 30, 32 of the first mechanism 12 are substantially aligned with the respective longitudinal axes 134, 164, 212 of the links 124, 126, 128 of the second mechanism, and the second end 26 of the first mechanism 12 is at substantially the same position as the second end 122 of the second mechanism 14. A tensioning cable is pulled tight, thereby placing the first mechanism 12 in the rigid mode. The steering cables are not pulled tight, thereby placing the second mechanism 14 in the limp mode.

The second mechanism 14 is then advanced so that its second link 126 is positioned approximately one link ahead of the second end 24 of the first mechanism 12 as shown in step "b" of FIG. 10. The cables 16, 18, 20 may be utilized to orient the second link 126 to a particular orientation, where the longitudinal axis 134 of the first link 124 is no longer aligned with the longitudinal axes 164 of the intermediate links 128 of the second mechanism 14 or the longitudinal axis 90 of the second link 30 of the first mechanism 12. After the second link 126 is in the desired position and orientation, the steering cables are pulled with identical force in order to place the second mechanism 14 in the rigid mode, thereby preserving the position and orientation of the second mechanism 14.

The pulling force of the tensioning cable is then released to place the first mechanism 12 in the limp mode. After the first mechanism 12 is placed in the limp mode, the first mechanism 12 is advanced so that its second link 30 is at substantially the same position as the second end 122 of the second mechanism 14 as shown in step "c" of FIG. 10. After the second link 30 of the first mechanism 12 is in the desired position and orientation, the tensioning cable is pulled tight to place the first mechanism 12 back in the rigid mode, thereby preserving the position and orientation of the first mechanism 12.

The pulling forces of the steering cables are then released to place the second mechanism 14 back in the limp mode. After the second mechanism 14 is placed back in the limp mode, the second mechanism 14 is advanced so that its second link 126 is once again positioned approximately one link ahead of the second end 26 of the first mechanism 12 as shown in step "d" of FIG. 10. After the second link 126 is in the desired position and orientation, the steering cables are pulled with identical force in order to place the second mechanism 14 in the rigid mode, thereby preserving the position and orientation of the second mechanism 14.

The pulling force of the tensioning cable is then released to place the first mechanism 12 back in the limp mode. After the first mechanism 12 is placed back in the limp mode, the first mechanism 12 is advanced so that its second link 30 is once again at substantially the same position as the second end 122 of the second mechanism 14 as shown in step "e" of FIG. 10. After the second link 30 of the first mechanism 12 is in the desired position and orientation, the tensioning cable is pulled tight to place the first mechanism 12 back in the rigid mode, thereby preserving the position and orientation of the first mechanism 12. The general motion sequence described hereinabove, may be repeated any number of times, and the second link 126 of the second mechanism 14 may be advancing in any direction and orientation. One skilled in the art will appreciate that any number of motion sequences may be utilized with the multi-linked device 10. For example, according to various embodiments, the second mechanism 14 may advance any number of links ahead of the first mechanism 12.

The exemplary sizes described hereinabove are generally relative to each other, and one skilled in the art will appreciate that the multi-linked device 10 can be scaled up or scaled down. For example, although the diameter at the largest portion of the intermediate link 128 of the multi-linked device 10 is on the order of approximately 9.65 millimeters for the embodiments described hereinabove, one skilled in the art will appreciate that, for other embodiments, the intermediate link 128 can be scaled down such that the diameter at the largest portion of the intermediate link 128 of the multi-linked device 10 is on the order of approximately 1.0 millimeter. For such embodiments, each of the other components of the multi-linked device 10 would also be proportionally scaled down.

Figure 11:
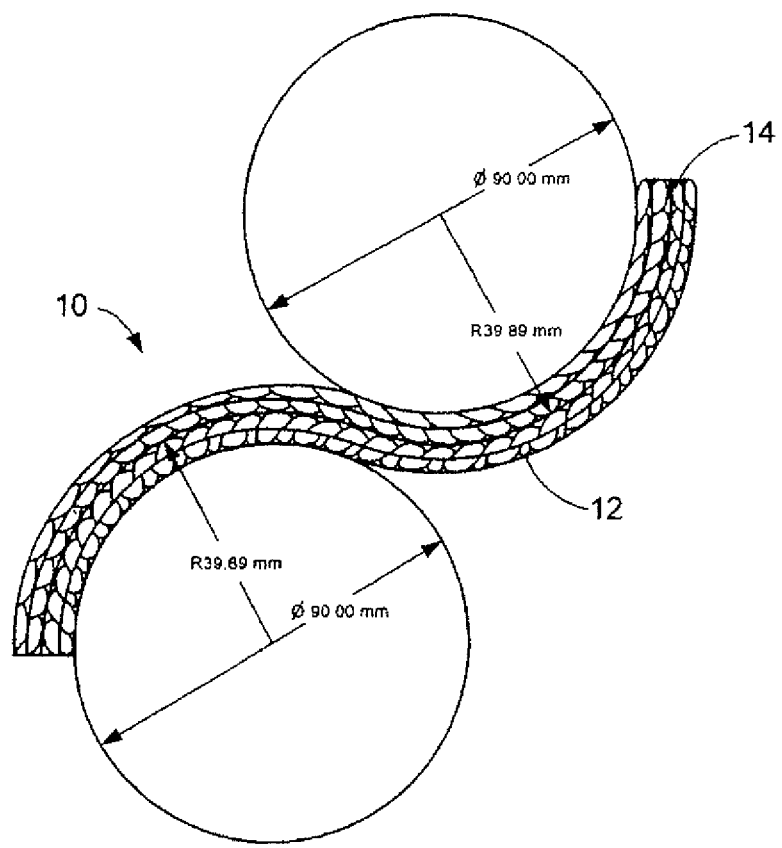
FIG. 11 illustrates various embodiments of a steerable multi-linked device traversing a path having tight curvatures.

The combination of the unique configuration of the respective links 28, 30, 32 which comprise the first mechanism 12 and the unique configuration of the respective links 124, 126, 128 which comprise the second mechanism 14 provides the multi-linked device 10 with the ability to traverse a path defined by the circumference of a circle having a relatively small radius. For example, for the exemplary sizes described hereinabove, the multi-linked device 10 can traverse a path defined by the circumference of a circle having a radius on the order of approximately 45 millimeters. An example of the multi-linked device 10 navigating such tight curvatures is shown in FIG. 11. For embodiments, where the largest portion of the intermediate link 128 of the multi-linked device 10 is on the order of approximately 1.0 millimeter, the multi-linked device 10 can traverse a path defined by the circumference of a circle having a radius significantly smaller than 45 millimeters. One skilled in the art will appreciate that the ability to navigate such tight curvatures makes the multi-linked device 10 suitable for use in a number of different minimally invasive procedures, both in luminal spaces and in intracavity spaces.

Figure 12A:
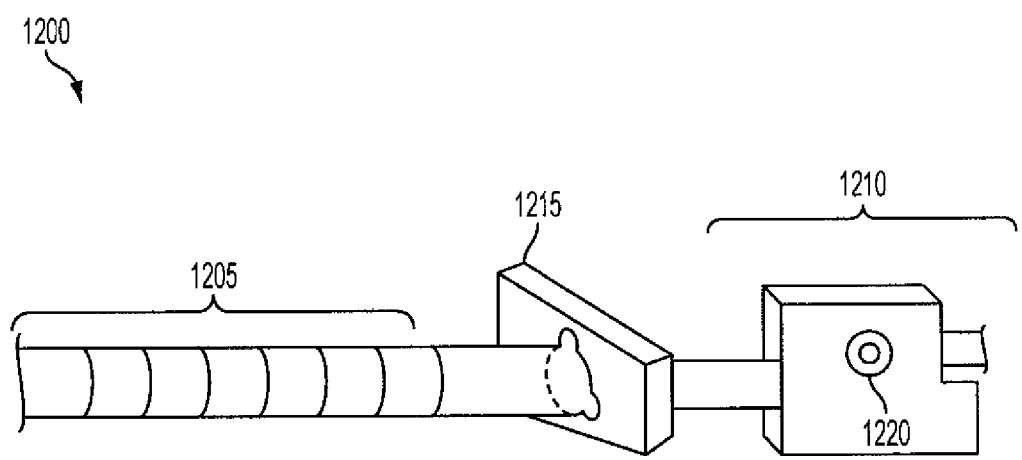
FIG. 12A illustrates various embodiments of a system for releasably attaching a steerable disposable multi-linked device to a durable device.

FIG. 12A illustrates various embodiments of a system 1200 for releasably attaching a steerable disposable multi-linked device 10 to a durable device according to an embodiment. The system 1200 may include one or more of a disposable portion 1205, a durable portion 1210 and a connecting member 1215. In various embodiments, the disposable portion 1205 may include the multi-linked device 10 such as that described in the previous drawings and accompanying text.

Figure 12B:
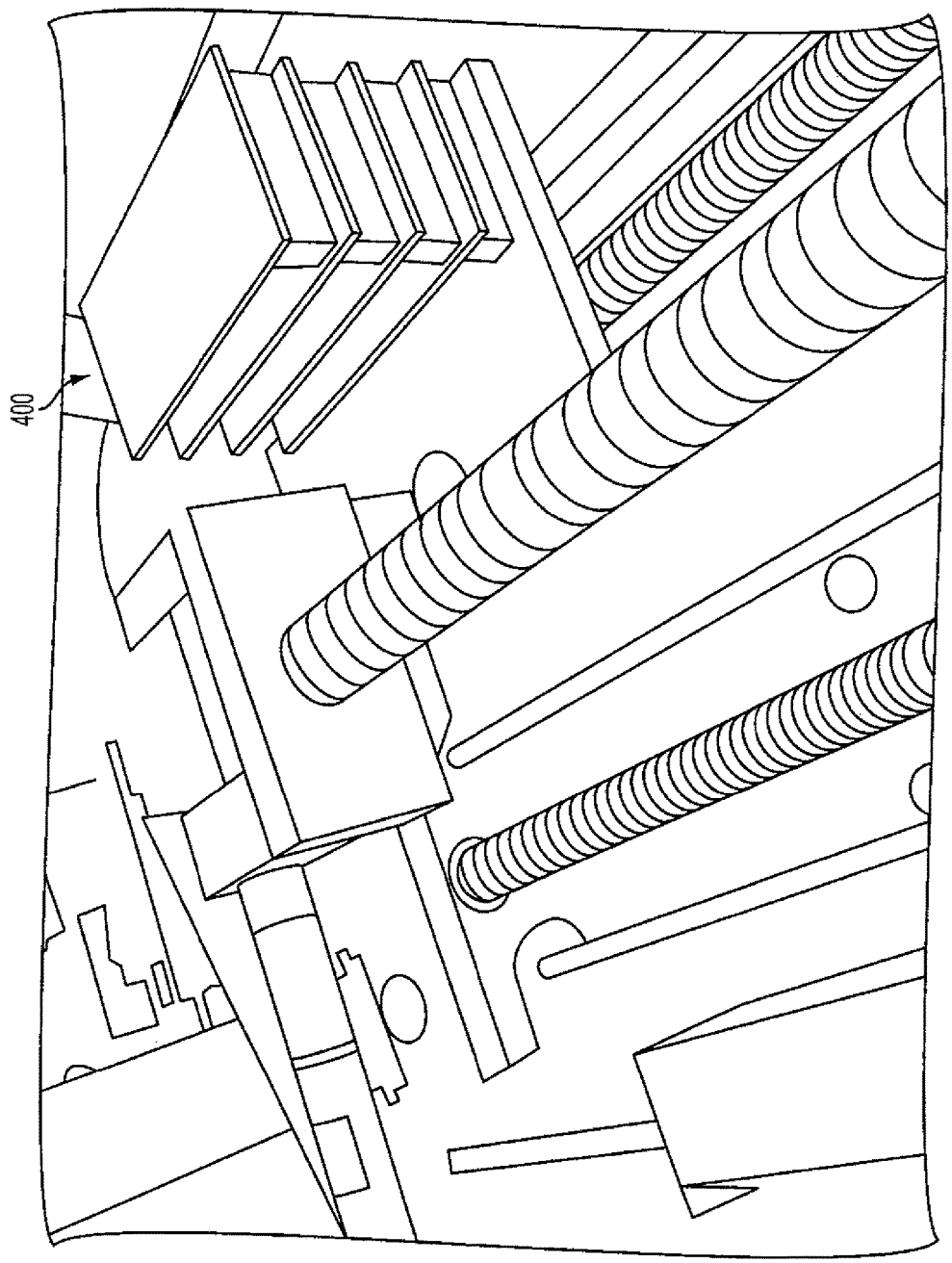
FIG. 12B illustrates various embodiments of a feeder mechanism.
Figure 13A:
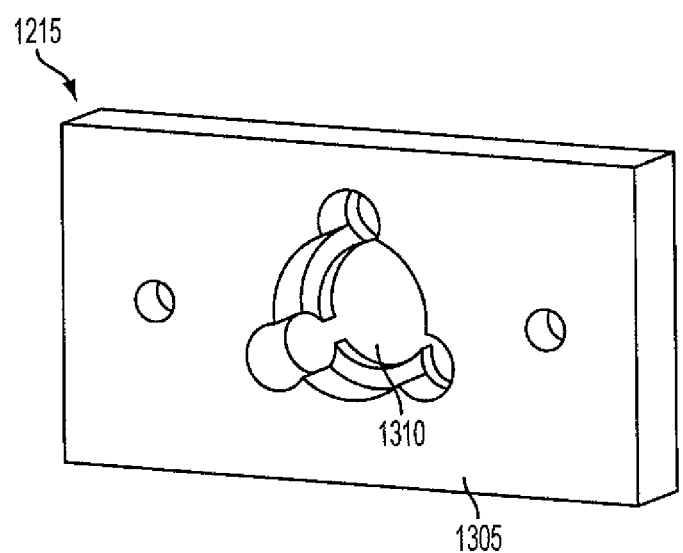
FIGS. 13A-13D illustrate an exemplary connecting member according to various embodiments.
Figure 13B:
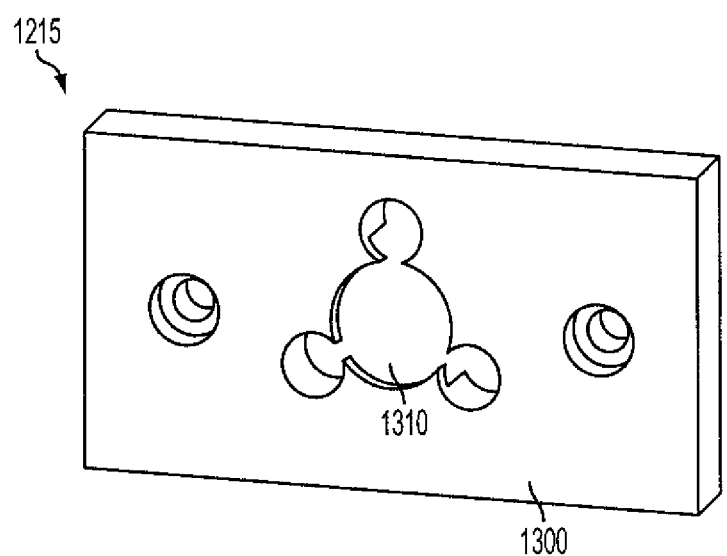
Figure 13C:
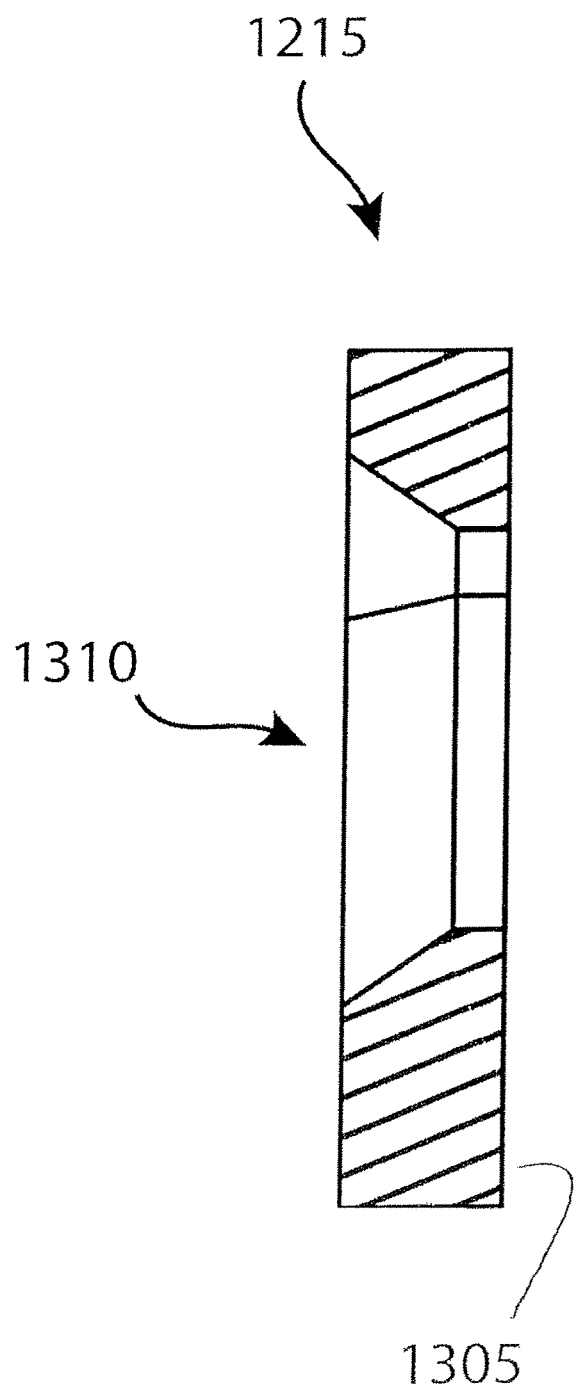
Figure 13D:
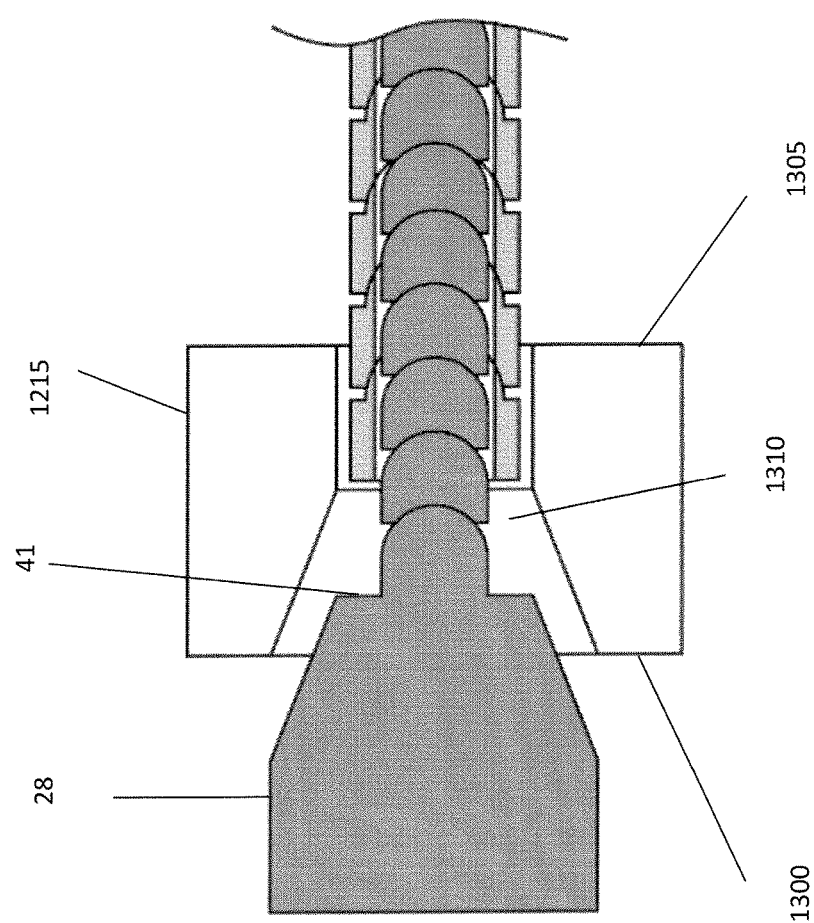

Referring to FIG. 12A, according to various embodiments, the disposable portion 1205 may include the connecting member 1215. In various embodiments, the durable portion 1210 may include a feeder mechanism 400, such as that illustrated in FIG. 12B, and/or other similar devices. The feeder mechanism 400 may include circuitry, motors and/or the like which cooperate to control the movement of the device 10. In various embodiments, the feeder mechanism 400 may operate to advance, retract, position and/or steer the first and/or second mechanisms (12, 14 of FIG. 1) of the device 10 in three dimensions.

In various embodiments, the disposable portion 1205 may be connected to the durable portion 1210 in any suitable manner. For example, the device 10 may be removably connected to the feeder mechanism 400 in a manner which facilitates the quick attachment or detachment of the device 10 from the feeder mechanism 400. In various embodiments, the durable portion 1210 may be connected to the disposable portion 1205 via the connecting member 1215. In various embodiments, the connecting member 1215 may be connected to the disposable portion 1205 and the durable portion 1210 in any suitable manner. For example, the connecting member 1215 may be connected to the feeder mechanism 400 via one or more screws, a snap-fit connection or the like.

FIGS. 13A-13D illustrate an exemplary connecting member 1215 according to an embodiment. The connecting member 1215 includes a first end 1300 and a second end 1305. The connecting member 1215 defines an opening 1310 therewith extending from the first end 1300 to the second end 1305 of the connecting member 1215. The opening 1310 is of a sufficient size to allow the device 10 to pass therethrough, and one or more intermediate links 128 may pass through the opening 1310. The opening 1310 may taper from the first end 1300 of the connecting member 1215 toward the second end 1305 of the connecting member 1215, as illustrated, for example, in FIG. 13C. According to various embodiments, the reduction in diameter of the opening 1310 may be used to capture a flange, rim, collar or the like 41 on an end of the first link 28 (e.g., the proximal link) to secure the disposable portion 1205 to the durable portion 1210.

Figure 14A:
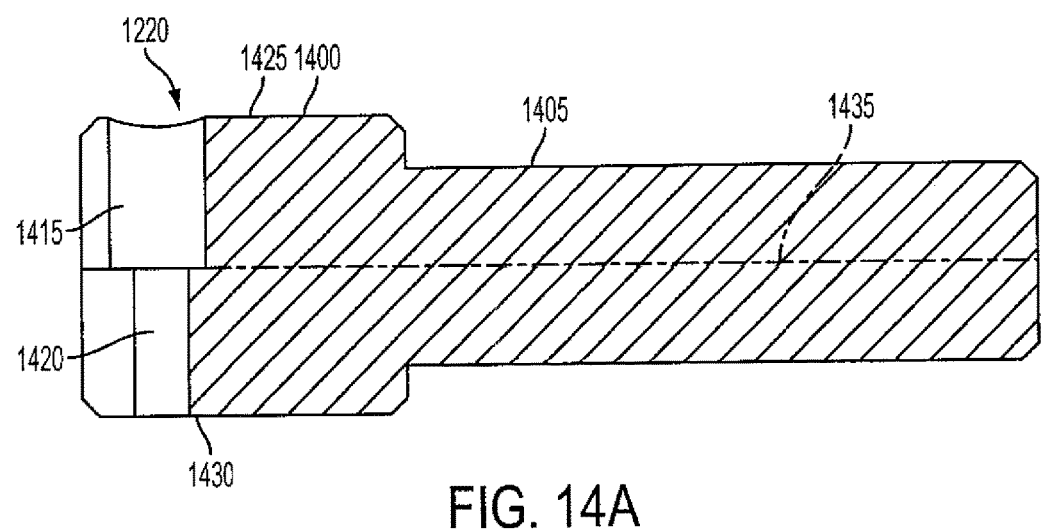
Figure 14C:
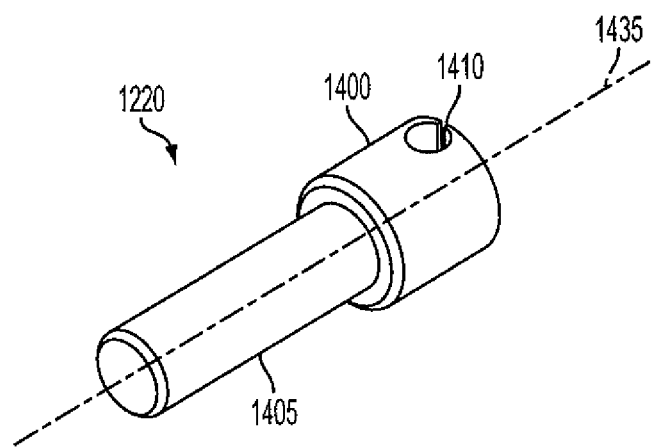

In various embodiments, the durable portion may include an axial member 1220 such as that illustrated in FIGS. 14A-14C. According to various embodiments, the axial member 1220 includes a first portion 1400 and a second portion 1405. The first portion 1400 of the axial member 1220 may be connected to the second portion 1405 of the axial member 1220 in any suitable manner. The second portion 1405 of the axial member 1220 may be connected to a motor 1440. In various embodiments, the axial member 1220 may be a screw, a drum or the like.

The axial member 1220 defines an opening 1410 therethrough. In various embodiments, the opening 1410 may include a first portion 1415 and a second portion 1420. The first portion 1415 of the opening 1410 may be proximate to a first end 1425 of the axial member 1220. The second portion 1420 of the opening 1410 may be proximate to a second end 1430 of the axial member 1220 and may be adjacent to the first portion 1415. In various embodiments, a cross-section of the first portion 1415 along a longitudinal axis 1435 may be larger than a cross-section of the second portion 1420 along the longitudinal axis 1435.

In various embodiments, one or more cables 1445 of the device 10 may pass through the first link 28 and one or more of the intermediate links 32 and may extend beyond the first end (e.g., the proximal end) of the first link 28. The cables 1445 may include a knot or other similar stopper 1450 at one end thereof. The cables 1445 may be positioned in the opening 1410 of the axial member 1220 such that the cables are secured to the axial member 1220.

In various embodiments, the disposable portion 1205 may be sterilizable. In various embodiments, the device 10 may be utilized as a disposable device. After the device 10 is disconnected from the durable portion 1205, another device 10 may be quickly connected to the durable portion 1205.

While several embodiments of the invention have been described herein by way of example, those skilled in the art will appreciate that various modifications, alterations, and adaptations to the described embodiments may be realized without departing from the spirit and scope of the invention defined by the appended claims.

What is claimed is:

1. A system for releasably attaching a steerable disposable multi-linked device to a durable device, the system comprising:
   a disposable portion;
   a durable portion; and
   a connecting member connecting the disposable portion and the durable portion, wherein the connecting member defines an opening extending from a first end of the connecting member toward a second end of the connecting member, wherein the opening tapers from the first end of the connecting member toward the second end of the connecting member,
   wherein, the disposable portion comprises:
      a steerable multi-linked device, comprising:
         a first multi-linked mechanism comprising:
            a first link comprising a flange, wherein the opening of the connecting member is configured to capture the flange,
            a plurality of intermediate links, wherein a first one of the intermediate links is movably coupled to the first link, and
            a second link movably coupled to a second one of the intermediate links; and
         a second multi-linked mechanism,
         wherein the second multi-linked mechanism is configured to surround at least a portion of the first multi-linked mechanism,
   wherein, the durable portion comprises:
      an axial member which defines an opening therethrough, and
      a feeder mechanism configured to advance, retract or advance and retract the second multi-linked mechanism relative to the feeder mechanism, and through the opening of the connecting member.

2. The system of claim 1, wherein the opening of the axial member defines:
   a first portion proximate a first end of the axial member; and
   a second portion proximate a second end of the axial member, wherein the second portion is adjacent to the first portion, wherein a cross-section of the first portion along a longitudinal axis is greater than a cross-section of the second portion along the longitudinal axis.

3. The system of claim 1, wherein the axial member comprises a first portion and a second portion, wherein the second portion is connected to the first portion, wherein the second portion is coupled to a motor.

4. The system of claim 1, wherein:
   the first link, the second link and the intermediate links define a first plurality of grooves,
   the second multi-linked mechanism comprises a second plurality of grooves, and
   the first and second pluralities of grooves cooperate to define at least two working ports along a length of the multi-linked device.

5. The system of claim 1, wherein the first multi-linked mechanism comprises a passage through which a cable passes.

6. The system of claim 5, wherein a cable passes through the opening of the axial member.

7. The system of claim 6, wherein the cable comprises a stopper at an end of the cable.

* * * * *